(12) United States Patent
Euteneuer et al.

(10) Patent No.: US 9,693,902 B2
(45) Date of Patent: *Jul. 4, 2017

(54) METHODS AND APPARATUS FOR TREATING GLAUCOMA

(71) Applicant: IVANTIS, INC., Irvine, CA (US)

(72) Inventors: Charles L. Euteneuer, St. Michael, MN (US); Thomas R. Hektner, Medina, MN (US); Andrew T. Schieber, Irvine, CA (US); John Wardle, San Clemente, CA (US)

(73) Assignee: IVANTIS, INC., Irvine, CA (US)

( * ) Notice: Subject to any disclaimer, the term of this patent is extended or adjusted under 35 U.S.C. 154(b) by 103 days.

This patent is subject to a terminal disclaimer.

(21) Appl. No.: 14/717,744

(22) Filed: May 20, 2015

(65) Prior Publication Data

US 2015/0250649 A1    Sep. 10, 2015

Related U.S. Application Data

(60) Continuation of application No. 13/968,051, filed on Aug. 15, 2013, now Pat. No. 9,066,783, which is a
(Continued)

(51) Int. Cl.
*A61F 9/007* (2006.01)
*A61F 9/00* (2006.01)
(Continued)

(52) U.S. Cl.
CPC ........ *A61F 9/00781* (2013.01); *A61F 9/0017* (2013.01); *A61F 9/007* (2013.01);
(Continued)

(58) Field of Classification Search
CPC .. A61F 2009/00885; A61F 2009/00891; A61F 9/0017; A61F 9/007;
(Continued)

(56) References Cited

U.S. PATENT DOCUMENTS

| 703,296 A | 6/1902 | Arnold |
| 1,601,709 A | 10/1926 | Windom |

(Continued)

FOREIGN PATENT DOCUMENTS

| AU | 1998/76197 B2 | 2/1999 |
| CN | 1950091 A | 4/2007 |

(Continued)

OTHER PUBLICATIONS

Schieber et al.; U.S. Appl. No. 15/012,544 entitled "Methods and devices for increasing aqueous humor outflow," filed Feb. 1, 2016.
(Continued)

*Primary Examiner* — Adam Marcetich
(74) *Attorney, Agent, or Firm* — Shay Glenn LLP

(57) ABSTRACT

An ocular implant for treating glaucoma is provided, which may include any number of features. More particularly, the present invention relates to implants that facilitate the transfer of fluid from within one area of the eye to another area of the eye. One feature of the implant is that it includes a proximal inlet portion and a distal inlet portion adapted to be inserted into the anterior chamber of the eye, and an intermediate portion adapted to be inserted into Schlemm's canal. Another feature of the implant is that it can be biased to assume a predetermined shape to aid in placement within the eye.

13 Claims, 17 Drawing Sheets

Related U.S. Application Data division of application No. 13/610,769, filed on Sep. 11, 2012, now Pat. No. 8,529,494, which is a continuation of application No. 12/398,847, filed on Mar. 5, 2009, now Pat. No. 8,267,882.

(60) Provisional application No. 61/034,059, filed on Mar. 5, 2008.

(51) Int. Cl.
 *A61F 9/008* (2006.01)
 *A61K 9/00* (2006.01)
 *A61M 27/00* (2006.01)

(52) U.S. Cl.
 CPC .......... *A61F 2009/00885* (2013.01); *A61F 2009/00891* (2013.01); *A61K 9/0051* (2013.01); *A61M 27/002* (2013.01); *A61M 2210/0612* (2013.01); *Y10S 623/905* (2013.01); *Y10S 623/906* (2013.01)

(58) Field of Classification Search
 CPC ........ A61F 9/00781; A61F 2009/00865; A61F 9/0008; A61K 9/0051; A61M 2210/0612; A61M 27/002; Y10S 623/905; Y10S 623/906
 See application file for complete search history.

(56) References Cited

U.S. PATENT DOCUMENTS

| | | |
|---|---|---|
| 2,716,983 A | 9/1955 | George et al. |
| 3,071,135 A | 1/1963 | Baldwin et al. |
| 3,788,327 A | 1/1974 | Donowitz et al. |
| 3,811,442 A | 5/1974 | Maroth |
| 3,948,271 A | 4/1976 | Akiyama |
| 4,037,604 A | 7/1977 | Newkirk |
| 4,134,405 A | 1/1979 | Smit |
| 4,428,746 A | 1/1984 | Mendez |
| 4,457,757 A | 7/1984 | Molteno |
| 4,601,713 A | 7/1986 | Fuqua |
| 4,604,087 A | 8/1986 | Joseph |
| 4,689,040 A | 8/1987 | Thompson |
| 4,699,140 A | 10/1987 | Holmes et al. |
| 4,706,669 A | 11/1987 | Schlegel |
| 4,722,724 A | 2/1988 | Schocket |
| 4,733,665 A | 3/1988 | Palmaz |
| 4,750,901 A | 6/1988 | Molteno |
| 4,826,478 A | 5/1989 | Schocket |
| 4,861,341 A | 8/1989 | Woodburn |
| 4,880,000 A | 11/1989 | Holmes et al. |
| 4,886,488 A | 12/1989 | White |
| 4,919,130 A | 4/1990 | Stoy et al. |
| 4,934,363 A | 6/1990 | Smith et al. |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 5,092,837 A | 3/1992 | Ritch et al. |
| 5,127,901 A | 7/1992 | Odrich |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,246,452 A | 9/1993 | Sinnott |
| 5,290,267 A | 3/1994 | Zimmermann |
| 5,360,399 A | 11/1994 | Stegmann |
| 5,372,577 A | 12/1994 | Ungerleider |
| 5,445,637 A | 8/1995 | Bretton |
| 5,454,796 A | 10/1995 | Krupin |
| 5,458,615 A | 10/1995 | Klemm et al. |
| 5,536,259 A | 7/1996 | Utterberg |
| 5,575,780 A | 11/1996 | Saito |
| 5,591,223 A | 1/1997 | Lock et al. |
| 5,613,972 A | 3/1997 | Lee et al. |
| 5,626,558 A | 5/1997 | Suson |
| 5,653,753 A | 8/1997 | Brady et al. |
| 5,676,669 A | 10/1997 | Colvard |
| 5,792,099 A | 8/1998 | DeCamp et al. |
| 5,807,302 A | 9/1998 | Wandel |
| 5,865,831 A | 2/1999 | Cozean et al. |
| 5,868,697 A | 2/1999 | Richter et al. |
| 5,879,319 A | 3/1999 | Pynson et al. |
| 5,893,837 A | 4/1999 | Eagles et al. |
| 5,919,171 A | 7/1999 | Kira et al. |
| 5,948,427 A | 9/1999 | Yamamoto et al. |
| 5,968,058 A | 10/1999 | Richter et al. |
| 6,007,511 A | 12/1999 | Prywes |
| 6,050,970 A | 4/2000 | Baerveldt |
| 6,102,045 A | 8/2000 | Nordquist et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| 6,241,721 B1 | 6/2001 | Cozean et al. |
| D444,874 S | 7/2001 | Haffner et al. |
| 6,328,747 B1 | 12/2001 | Nun |
| 6,375,642 B1 | 4/2002 | Grieshaber et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,551,289 B1 | 4/2003 | Higuchi et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,702,790 B1 | 3/2004 | Ross |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,899,717 B2 | 5/2005 | Weber et al. |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,094,225 B2 | 8/2006 | Tu et al. |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,123,729 B2 | 2/2012 | Yamamoto et al. |
| 8,172,899 B2 | 5/2012 | Silvestrini et al. |
| 8,267,882 B2 | 9/2012 | Euteneuer et al. |

(56) References Cited

U.S. PATENT DOCUMENTS

| | | |
|---|---|---|
| 8,282,592 B2 | 10/2012 | Schieber et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,512,404 B2 | 8/2013 | Frion et al. |
| 8,529,494 B2 | 9/2013 | Euteneuer et al. |
| 8,551,166 B2 | 10/2013 | Schieber et al. |
| 8,657,776 B2 | 2/2014 | Wardle et al. |
| 8,663,150 B2 | 3/2014 | Wardle et al. |
| 8,734,377 B2 | 5/2014 | Schieber et al. |
| 8,808,222 B2 | 8/2014 | Schieber et al. |
| 8,945,038 B2 | 2/2015 | Yablonski |
| 8,961,447 B2 | 2/2015 | Schieber et al. |
| 9,039,650 B2 | 5/2015 | Schieber et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0026200 A1* | 2/2002 | Savage ............... A61F 9/00781 606/108 |
| 2002/0052653 A1 | 5/2002 | Durgin |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0193805 A1 | 12/2002 | Ott et al. |
| 2003/0004457 A1 | 1/2003 | Andersson |
| 2003/0040754 A1 | 2/2003 | Mitchell et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |
| 2003/0125351 A1 | 7/2003 | Azuma et al. |
| 2003/0181848 A1 | 9/2003 | Bergheim et al. |
| 2003/0187384 A1 | 10/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0082939 A1 | 4/2004 | Berlin |
| 2004/0088048 A1 | 5/2004 | Richter et al. |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0122380 A1 | 6/2004 | Utterberg |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0199171 A1 | 10/2004 | Akahoshi |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0244464 A1 | 11/2005 | Hughes |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0178674 A1 | 8/2006 | McIntyre |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0241749 A1 | 10/2006 | Tu et al. |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0135681 A1 | 6/2007 | Chin et al. |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0219509 A1 | 9/2007 | Tashiro et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0228127 A1 | 9/2008 | Burns et al. |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |

(56) References Cited

U.S. PATENT DOCUMENTS

| | | |
|---|---|---|
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082862 A1 | 3/2009 | Schieber et al. |
| 2009/0104248 A1 | 4/2009 | Rapacki et al. |
| 2009/0138081 A1 | 5/2009 | Bergheim et al. |
| 2009/0182421 A1 | 7/2009 | Silvestrini et al. |
| 2009/0198248 A1 | 8/2009 | Yeung et al. |
| 2009/0204053 A1 | 8/2009 | Nissan et al. |
| 2009/0247955 A1 | 10/2009 | Yamamoto et al. |
| 2009/0259126 A1 | 10/2009 | Saal et al. |
| 2009/0281520 A1 | 11/2009 | Highley et al. |
| 2010/0004580 A1 | 1/2010 | Lynch et al. |
| 2010/0057072 A1 | 3/2010 | Roman et al. |
| 2010/0114309 A1 | 5/2010 | de Juan et al. |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0234726 A1 | 9/2010 | Sirimanne et al. |
| 2010/0234790 A1 | 9/2010 | Tu et al. |
| 2011/0009874 A1 | 1/2011 | Wardle et al. |
| 2011/0098809 A1 | 4/2011 | Wardle et al. |
| 2011/0224597 A1 | 9/2011 | Stegmann et al. |
| 2011/0319806 A1 | 12/2011 | Wardle |
| 2012/0010702 A1 | 1/2012 | Stegmann et al. |
| 2013/0150959 A1 | 6/2013 | Schieber et al. |
| 2013/0182223 A1 | 7/2013 | Wardle et al. |
| 2013/0231603 A1 | 9/2013 | Wardle et al. |
| 2013/0281907 A1 | 10/2013 | Wardle et al. |
| 2014/0066821 A1 | 3/2014 | Friedland et al. |
| 2014/0066831 A1 | 3/2014 | Silvestrini et al. |
| 2014/0114229 A1 | 4/2014 | Wardle et al. |
| 2014/0249463 A1 | 9/2014 | Wardle et al. |
| 2015/0119787 A1 | 4/2015 | Wardle et al. |
| 2016/0051406 A1 | 2/2016 | Wardle et al. |

FOREIGN PATENT DOCUMENTS

| | | |
|---|---|---|
| DE | 4226476 C1 | 8/1993 |
| EP | 0168201 B1 | 6/1988 |
| EP | 0766544 B1 | 5/1998 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| JP | H10-504978 A | 5/1998 |
| JP | 11123205 | 5/1999 |
| JP | 2002542872 | 12/2002 |
| JP | 2006517848 | 8/2006 |
| JP | 2006289075 A | 10/2006 |
| JP | 2010509003 | 3/2010 |
| JP | 2011502649 | 1/2011 |
| WO | WO 00/07525 A1 | 2/2000 |
| WO | WO 00/64389 A1 | 11/2000 |
| WO | WO 00/64393 A1 | 11/2000 |
| WO | WO 01/97727 A1 | 12/2001 |
| WO | WO 02/36052 A1 | 5/2002 |
| WO | WO 02/074052 A2 | 9/2002 |
| WO | WO 02/080811 A2 | 10/2002 |
| WO | WO 03/015659 A2 | 2/2003 |
| WO | WO 03/045290 A1 | 6/2003 |
| WO | WO 2004/054643 A1 | 7/2004 |
| WO | WO 2004/093761 A1 | 11/2004 |
| WO | WO 2005/105197 A2 | 11/2005 |
| WO | WO 2006/066103 A2 | 6/2006 |
| WO | WO 2007/035356 A2 | 3/2007 |
| WO | WO 2007/047744 A2 | 4/2007 |
| WO | WO 2007/087061 A2 | 8/2007 |
| WO | WO 2008/002377 A1 | 1/2008 |
| WO | WO 2008/005873 A2 | 1/2008 |
| WO | WO 2009/120960 A2 | 10/2009 |

OTHER PUBLICATIONS

Wardle et al.; U.S. Appl. No. 15/150,175 entitled "Ocular implants for delivery into an anterior chamber of the eye," filed May 9, 2016.

Bahler, et al.; Trabecular bypass stents decrease intraocular pressure in cultured human anterior segments; Amer. Journal of Ophthalmology; vol. 138, No. 6; pp. 988-994.e2; Dec. 2004.

D'Ermo, et al.; Our results with the operation of ab externo trabeculotomy; Ophthalmologica; vol. 163; pp. 347-355; Feb. 1971.

Ellingsen et al.; Trabeculotomy and sinusotomy in enucleated human eyes; Investigative Ophthalmology; vol. 11; pp. 21-28; Jan. 1972.

Grant; Experimental aqueous perfusion in enucleated human eyes; Archives of Ophthalmology; vol. 69; pp. 783-801; Jun. 1963.

Johnstone et al.; "Microsurgery of Schlemm's Canal and the Human Aqueous Outflow System;" American Journal of Ophthalmology, vol. 76 (6): 906-917; Dec. 1973.

Lee et al.; Aqueous-venous shunt and intraocular pressure. Preliminary report of animal studies; Investigative Ophthalmology; vol. 5; No. 1; pp. 59-64; Feb. 1966.

Lynch, Mary G.; U.S. Appl. No. 60/131,030 entitled "Devices and methods for treating glaucoma by enhancing aqueous outflow through schlemm's canal and anterior chamber angle ," filed Apr. 26, 1999.

Moses, Robert; The effect of intraocular pressure on resistance to outflow; Survey of Ophthalmology; vol. 22; No. 2; pp. 88-100; Sep.-Oct. 1977.

Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.

Rosenquist et al.; Outflow resistance of enucleated human eyes at two different perfusion pressures and different extents of trabeculotomy; Current Eye Res.; vol. 8, No. 12; pp. 1233-1240; Dec. 1989.

Savage, James; Gonioscopy in the management of glaucoma; Am. Academy of Ophthalmology; Focal Points; vol. XXIV; No. 3; pp. 1-14; Mar. 2006.

Schultz, Jared; Canaloplasty procedure shows promise for open-angle glaucoma in European study; Ocular Surgery News; vol. 34; Mar. 1, 2007.

Smit et al.; Effects of viscoelastic injection into schlemm's canal in primate and human eyes; J. Am. Academy of Ophthalmology; vol. 109; No. 4; pp. 786-792; Apr. 2002.

Spiegel et al.; Schlemm's canal implant: a new method to lower intraocular pressure in patients with POAG?; Ophthalmic Surgery and Lasers; vol. 30; No. 6; pp. 492-494; Jun. 1999.

Wardle et al.; U.S. Appl. No. 14/363,409 entitled "Delivering ocular implants into the eye," filed Jun. 6, 2014.

Schieber et al.; U.S. Appl. No. 14/691,267 entitled "Ocular implants with asymmetric flexibility," filed Apr. 20, 2015.

Schieber et al.; U.S. Appl. No. 14/692,442 entitled "Methods and apparatus for delivering ocular implants into the eye," filed Apr. 21, 2015.

Schieber et al.; U.S. Appl. No. 14/693,582 entitled "Methods and apparatus for delivering ocular implants into the eye," filed Apr. 22, 2015.

Schiber et al.; U.S. Appl. No. 14/440,610 entitled "Apparatus for delivering ocular implants into an anterior chamber of the eye," filed May 5, 2015.

Schieber et al.; U.S. Appl. No. 14/843,563 entitled "Ocular implants for delivery into the eye," filed Sep. 2, 2015.

Kirkness et al.; The Use of Silicone Drainage Tubing to Control Post-Keratoplasty Glaucoma; Eye; 2 (pt 5); pp. 583-590; Apr. 1988.

Molteno et al.; Long Tube Implants in the Management of Glaucoma; SA Medical Journal; 26; pp. 1062-1066; Jun. 1976.

Molteno; New implant for drainage in glaucoma; Brit. J. Ophthal; 53; pp. 606-615; Sep. 1969.

(56) References Cited

OTHER PUBLICATIONS

Schocket et al.; Anterior Chamber Tube Shunt to an Encircling Band in the Treatment of Neovascular Glaucoma and other Refractory Glaucomas; Ophthalmology; 92; pp. 553-562; Apr. 1985.
Wilcox et al.; Hypothesis for Improving Accessory Filtration by Using Geometry; Journal of Glaucoma; 3; pp. 244-247; Fall 1994.

* cited by examiner

METHODS AND APPARATUS FOR TREATING GLAUCOMA

CROSS REFERENCE TO RELATED APPLICATIONS

This application is a continuation of U.S. application Ser. No. 13/968,051, filed Aug. 15, 2013, which application is a divisional of U.S. application Ser. No. 13/610,769, filed Sep. 11, 2012, now U.S. Pat. No. 8,529,494; which application is a continuation of U.S. application Ser. No. 12/398,847, filed Mar. 5, 2009, now U.S. Pat. No. 8,267,882; which application claims the benefit under 35 U.S.C. 119 of U.S. Provisional Patent Application No. 61/034,059, filed Mar. 5, 2008, titled "METHODS AND APPARATUS FOR TREATING GLAUCOMA." These applications are herein incorporated by reference.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to devices that are implanted within the eye. More particularly, the present invention relates to devices that facilitate the transfer of fluid from within one area of the eye to another area of the eye.

BACKGROUND

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," Investigative Ophthalmology (February 1966)). Other early glaucoma treatment implants led from the anterior chamber to a sub-conjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" Ophthalmic Surgery and Lasers (June 1999); U.S. Pat. Nos. 6,450,984; 6,450,984).

SUMMARY OF THE DISCLOSURE

The present invention relates to devices implanted within the eye. In one embodiment, an ocular implant defines a generally cylindrical volume and comprises a proximal inlet portion at a proximal end of the implant, a distal inlet portion at a distal end of the implant, the distal inlet portion being biased to bend at a first radius of curvature, an intermediate portion positioned between the proximal inlet portion and the distal inlet portion, and a plurality of openings in the implant to facilitate fluidic flow laterally across the elongate implant. The implant can also define a lumen to facilitate fluidic flow longitudinally along the implant.

In some embodiments, an intermediate portion of the implant is biased to bend at a second radius of curvature. In one embodiment, the first radius of curvature is smaller than the second radius of curvature. In other embodiments, the second radius of curvature can approximate the curvature of Schlemm's canal.

In one embodiment, the proximal portion of the implant is biased to bend at a third radius of curvature. The third radius of curvature can be generally smaller than the second radius of curvature. In another embodiment, the third radius of curvature can be generally equal to the first radius of curvature.

In some embodiments, the plurality of openings in the implant extend over more than about 50% of an outer surface area of the implant.

Yet another embodiment includes an ocular implant defining a generally cylindrical volume, comprising a proximal inlet portion at a proximal end of the implant, the proximal inlet portion adapted to be positioned in an anterior chamber of the eye, a distal inlet portion at a distal end of the implant, the distal inlet portion adapted to be positioned in the anterior chamber of the eye, an intermediate portion positioned between the proximal and distal inlet portions, the intermediate portion adapted to be positioned in Schlemm's canal, and a plurality of openings in the implant to facilitate fluidic flow laterally across the implant. The implant can also define a lumen to facilitate fluidic flow longitudinally along the implant.

One embodiment includes an assembly, comprising an ocular implant defining an implant lumen, a core disposed in the implant lumen, a guide wire disposed in a guide wire lumen defined by the core, wherein the guide wire is biased to assume a predetermined at rest shape, the guide wire having a distal radius of curvature and a proximal radius of curvature when the guide wire is assuming the predetermined at rest shape, and wherein the proximal radius of curvature is greater than the distal radius of curvature.

In one embodiment, the assembly further comprises a cannula disposed about the ocular implant. In yet another embodiment, the assembly further comprises a luer fitting disposed in fluid communication with a lumen defined by the cannula.

In some embodiments, the proximal radius of curvature approximates the curvature of Schlemm's canal. In other embodiments, an intermediate portion of the ocular implant is biased to bend at a second radius of curvature. In one embodiment, the proximal radius of curvature of the guide wire can be generally equal to the second radius of curvature of the ocular implant.

In other embodiments, the ocular implant and the core urge the guide wire to assume a stressed shape that is different from the predetermined at rest shape. The stressed shape is generally straighter than the predetermined at rest shape.

In some embodiments, the implant comprises a first material and the core comprises a second material different from the first material. The first material and the second material typically comprise materials which provide a relatively low friction interface when placed in sliding contact with one another. The first material and the second material also typically comprise materials which are unlikely to gall when placed in sliding contact with one another. In one embodiment, the first material comprises a metallic material and the second material comprises a polymeric material.

In one embodiment, the guide wire comprises a first material and the core comprises a second material different from the first material. In another embodiment, the first material and the second material comprise materials which provide a relatively low friction interface when placed in sliding contact with one another. The first material and the second material typically comprise materials which are unlikely to gall when placed in sliding contact with one another. In one embodiment, the first material comprises a metallic material and the second material comprises a polymeric material.

In another embodiment, a device comprises an ocular implant comprising a body and a hatch, the body defining a body lumen and a longitudinal axis, the hatch defining a hatch lumen having a hatch axis, the hatch comprising an arm hingedly connecting the hatch to the body, the hatch having a first position in which the hatch is generally coaxial with the body, the hatch having a second position in which the hatch axis is skewed relative to the longitudinal axis of the body, and wherein the hatch is biased to assume the second position.

In one embodiment, the hatch is disposed in the first position, and the device further includes a core extending through the body lumen and the hatch lumen. In another embodiment, at least a portion of the hatch extends around a portion of the core across a radial span of more than 180 degrees. In one embodiment, the core causes the hatch to remain in the first position. In another embodiment, the hatch assumes the first position when the core is withdrawn from the hatch lumen.

Another embodiment of the invention includes an ocular implant comprising a proximal locking portion at a proximal end of the implant, a distal locking portion at a distal end of the implant, an intermediate portion extending between the proximal locking portion and the distal locking portion, the intermediate portion having a longitudinal axis that follows an arcuate path when the implant is assuming a relaxed shape, wherein the proximal locking portion is biased to extend in a first radially inward direction relative to the arcuate path of the longitudinal axis of the intermediate portion, and wherein the distal locking portion is biased to extend in a second radially inward direction relative to the arcuate path of the longitudinal axis of the intermediate portion.

In one embodiment, the first radially inward direction and the second radially inward direction intersect one another. In another embodiment, the first radially inward direction and the second radially both lead out of Schlemm's canal of an eye when the intermediate portion of the implant is disposed in Schlemm's canal of the eye.

In some embodiments, the implant is dimensioned so that the proximal locking portion and the distal locking portion will both extend through a wall of Schlemm's canal of an eye when the intermediate portion of the implant is disposed in Schlemm's canal of the eye.

The implant described can reduce the likelihood that the intermediate portion of the implant will migrate within Schlemm's canal of an eye when the proximal locking portion and the distal locking portion both extend through a wall of Schlemm's canal.

In some embodiments, the first radially inward direction and the second radially both lead out of Schlemm's canal of an eye when the longitudinal axis of the intermediate portion is coaxial with a longitudinal axis of Schlemm's canal. In another embodiment, a radius of curvature of the longitudinal axis of the intermediate portion approximates the curvature of Schlemm's canal when the implant is assuming the relaxed shape.

In yet another embodiment, a wall of the implant defines a plurality of openings in the implant to facilitate fluidic flow laterally across the implant. The implant can also define a lumen to facilitate fluidic flow longitudinally along the implant.

In one embodiment of the invention, an ocular implant defining a generally cylindrical volume comprises a proximal inlet portion at a proximal end of the implant, the proximal inlet portion adapted to be positioned in an anterior chamber of the eye, a distal inlet portion at a distal end of the implant, the distal inlet portion adapted to be positioned in a suprachoroidal space of the eye, an intermediate portion positioned between the proximal and distal inlet portions, and a plurality of openings in the implant to facilitate fluidic flow laterally across the implant. The plurality of openings in the implant can also facilitate fluidic flow longitudinally along the implant.

The present invention also relates to a method of treating glaucoma in an eye of a patient, comprising positioning a proximal inlet portion of an implant in an anterior chamber of the eye, positioning an intermediate portion of the implant in Schlemm's canal, positioning a distal inlet portion of the implant in the anterior chamber of the eye, allowing aqueous humor to flow from the anterior chamber through the implant into Schlemm's canal.

The allowing step can further comprise allowing aqueous humor to flow from the anterior chamber into the proximal and distal inlet portions, through the intermediate portion, and into Schlemm's canal.

In one embodiment, aqueous humor flows into Schlemm's canal through a plurality of openings in the implant.

In another embodiment, the proximal inlet portion of the implant can be spaced approximately 60 to 180 degrees from the distal inlet portion.

In yet another embodiment, aqueous humor can flow longitudinally along the implant. Aqueous humor can also flow laterally across the implant.

Yet another method of the present invention relates to a method of implanting a dual inlet ocular implant into an eye of a patient, comprising, inserting a cannula into an anterior chamber of the eye so that a distal tip of the cannula is in communication with Schlemm's canal, inserting a distal inlet portion of the implant through the cannula into Schlemm's canal, advancing the implant distally along Schlemm's canal until only a proximal inlet portion of the implant remains in the cannula, introducing the distal inlet portion of the implant into the anterior chamber of the eye from Schlemm's canal.

In one embodiment, the method further comprises removing the cannula from the anterior chamber of the eye leaving the proximal inlet portion of the implant in the anterior chamber of the eye.

In another embodiment, the introducing step comprises, advancing a tissue penetrating guide wire distally from the implant to penetrate into the anterior chamber of the eye from Schlemm's canal, advancing the implant over the guide wire to introduce the distal inlet portion of the implant into the anterior chamber of the eye from Schlemm's canal.

In an alternative embodiment, the introducing step comprises, making an incision from the anterior chamber of the eye into Schlemm's canal at a position near the distal inlet portion of the implant, allowing the distal inlet portion of the implant to assume a predetermined at rest shape which results in the distal inlet portion bending through the incision into the anterior chamber of the eye from Schlemm's canal.

In another embodiment, the proximal inlet portion is spaced approximately 60 to 180 degrees from the distal inlet portion.

In one embodiment, the method comprises inserting a core into a lumen defined by the implant, and inserting a guide wire into a guide wire lumen defined by the core. Sometimes the core is disposed in the lumen defined by the implant while the implant is advanced distally along Schlemm's canal. Other times the guide wire is disposed in the guide wire lumen defined by the core while the implant is advanced distally along Schlemm's canal.

In one embodiment, the introducing step comprises advancing a distal portion of the guide wire distally from the core to penetrate into the anterior chamber of the eye from Schlemm's canal, and advancing the implant off of the core and over the guide wire to introduce the distal inlet portion of the implant into the anterior chamber of the eye from Schlemm's canal.

In some embodiments, the distal portion of the guide wire is urged to assume a stressed shape when the distal portion of the guide wire is disposed in the guidewire lumen and the distal portion of the guide wire is free to assume a predetermined at rest shape when the distal portion of the guide wire is advanced distally from the core.

In other embodiments, the distal portion of the guide wire has a distal radius of curvature when the distal portion of the guide wire is free to assume a predetermined at rest shape.

In yet other embodiments, a proximal portion of the guide wire has a proximal radius of curvature and the proximal radius of curvature is generally greater than the distal radius of curvature. In some embodiments the proximal radius of curvature approximates the curvature of Schlemm's canal.

In some embodiments, the cannula can be flushed with a fluid. The flushing can be performed prior inserting a distal end of the cannula into the anterior chamber for preventing the introduction of air bubbles into the anterior chamber of the eye.

In other embodiments, a bolus of viscoelastic material can be injected proximate a target location in the anterior chamber of the eye. The method can further comprise piercing a wall of Schlemm's canal or a trabecular mesh with a distal end of the cannula at the target location. Alternatively, the bolus of viscoelastic material can be injected prior to piercing the wall of Schlemm's canal for precluding the formation of a pool of blood near the target location.

In one embodiment, the introducing step comprises advancing a self-piercing distal inlet in a distal direction to cause the distal inlet to cut through Schlemm's canal into the anterior chamber. The self-piercing distal inlet can be advanced while the distal inlet portion is biased inwards.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The following detailed description should be read with reference to the drawings, in which like elements in different drawings are numbered identically. The drawings, which are not necessarily to scale, depict exemplary embodiments and are not intended to limit the scope of the invention. Examples of constructions, materials, dimensions, and manufacturing processes are provided for selected elements. All other elements employ that which is known to those of skill in the field of the invention. Those skilled in the art will recognize that many of the examples provided have suitable alternatives that can be utilized.

Figure 1:
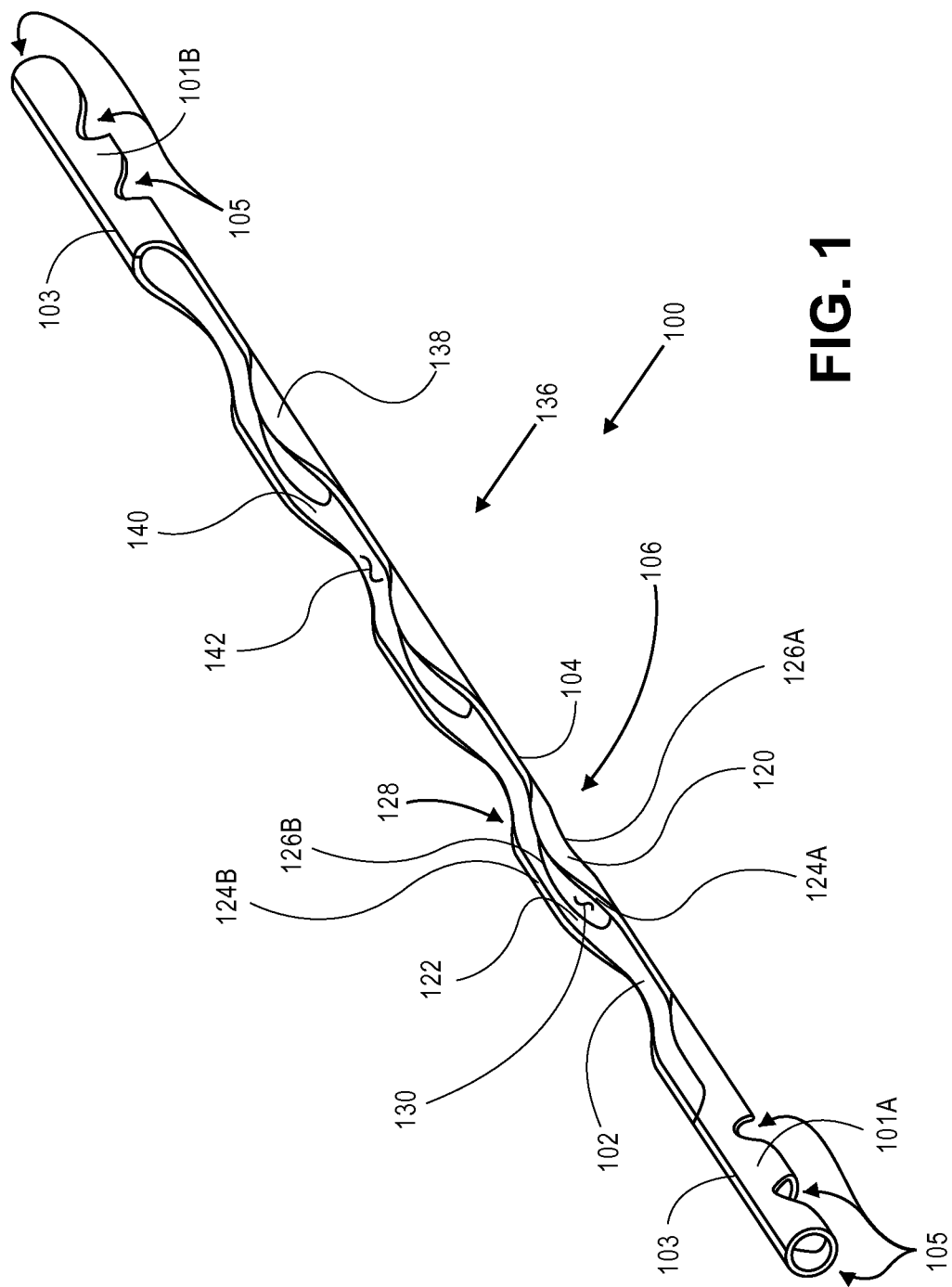
FIG. 1 is a schematic drawing of an ocular implant.

FIG. 1 is a schematic view of an implant 100 that may be used, for example, to facilitate the flow of aqueous humor within the eye of a patient. Implant 100 comprises spines 102 and 104 and a frame 106 disposed between the spines. In FIG. 1, frame 106 comprises a first strut 120 and a second strut 122. The struts extend between the spines. First strut 120 comprises a first edge 124A and a second edge 126A. Second strut 122 has a shape that is a mirror image of the shape of the first strut. Thus, the second strut comprises a first edge 124B and a second edge 126B. In FIG. 1, a first opening 128 is defined by the space between first edge 124A of first strut 120 and first edge 124B of second strut 122. Similarly, a second opening 130 is defined by the space between second edge 126A of first strut 120 and second edge 126B of second strut 122. The second opening generally divides the frame 106 into a first strut and a second strut. The openings defined by implant 100, such as first opening 128 and second opening 130, allow aqueous humor to flow laterally across and/or laterally through the implant.

Implant 100 typically comprises a plurality of spines and a plurality of frames. These spines and frames are arranged in an "ABAB" pattern. As shown in FIG. 1, implant 100 includes four spines and three frames, wherein each frame is positioned between adjacent spines. In other embodiments, the implant can have more or fewer spines and frames depending on the desired length and/or size of the implant. Implant 100 can be shaped to have an outer surface 138 defining a generally cylindrical volume. An inner surface 140 of the implant defines an elongate channel 142 or lumen to facilitate fluidic flow longitudinally along the implant. The plurality of spines and plurality of frames can be defined as an intermediate portion of the implant.

Implant 100 of FIG. 1 further comprises a proximal inlet portion 101A and a distal inlet portion 101B. Each inlet portion includes a plurality of apertures 105, to allow for fluid to flow into each inlet portion. The elongate channel 142 of implant 100 can fluidly communicate with the first and second inlet portions as well as first opening 128 and second opening 130 of the implant. As shown in FIG. 1, the intermediate portion of the implant can be positioned between the proximal and distal inlet portions.

Implant 100 may be inserted into Schlemm's canal of a human eye, for example, to facilitate the flow of aqueous humor out of the anterior chamber of the eye. Aqueous humor may flow, for example, into the proximal and distal inlet portions, through the intermediate portion of the implant, and into Schlemm's canal. Aqueous humor may exit Schlemm's canal via natural outlets communicating with the canal. The flow of aqueous humor may include axial flow along Schlemm's canal, flow from the anterior chamber into Schlemm's canal, flow leaving Schlemm's canal via natural outlets communicating with the canal, and flow through openings in the implant. When in place within the eye, the implant can support trabecular mesh tissue and Schlemm's canal tissue and can provide for improved communication between the anterior chamber and Schlemm's canal (via the trabecular meshwork) and between pockets or compartments along Schlemm's canal. The implant can facilitate flow of aqueous humor longitudinally along the implant, as well as laterally across the implant.

The outer diameter of the implant is selected to support the tissue of Schlemm's canal without undue stretching and is typically in the range of 0.005 inches to 0.04 inches, and preferably in the range of 0.005 inches to 0.02 inches. The arrangement of frames, spines, and openings along implant 100 support the tissue of Schlemm's canal with a minimum amount of material. In the embodiment shown in FIG. 1, for example, the openings (such as openings 128 and 130) extend over more than 50% of a tubular surface covering the volume of the portion of the implant lying within Schlemm's canal. This combination of features helps aqueous humor flow between any pockets or compartments formed within Schlemm's canal and, therefore, between the anterior chamber of the eye and the outlets from Schlemm's canal to the venous system.

Figure 2:
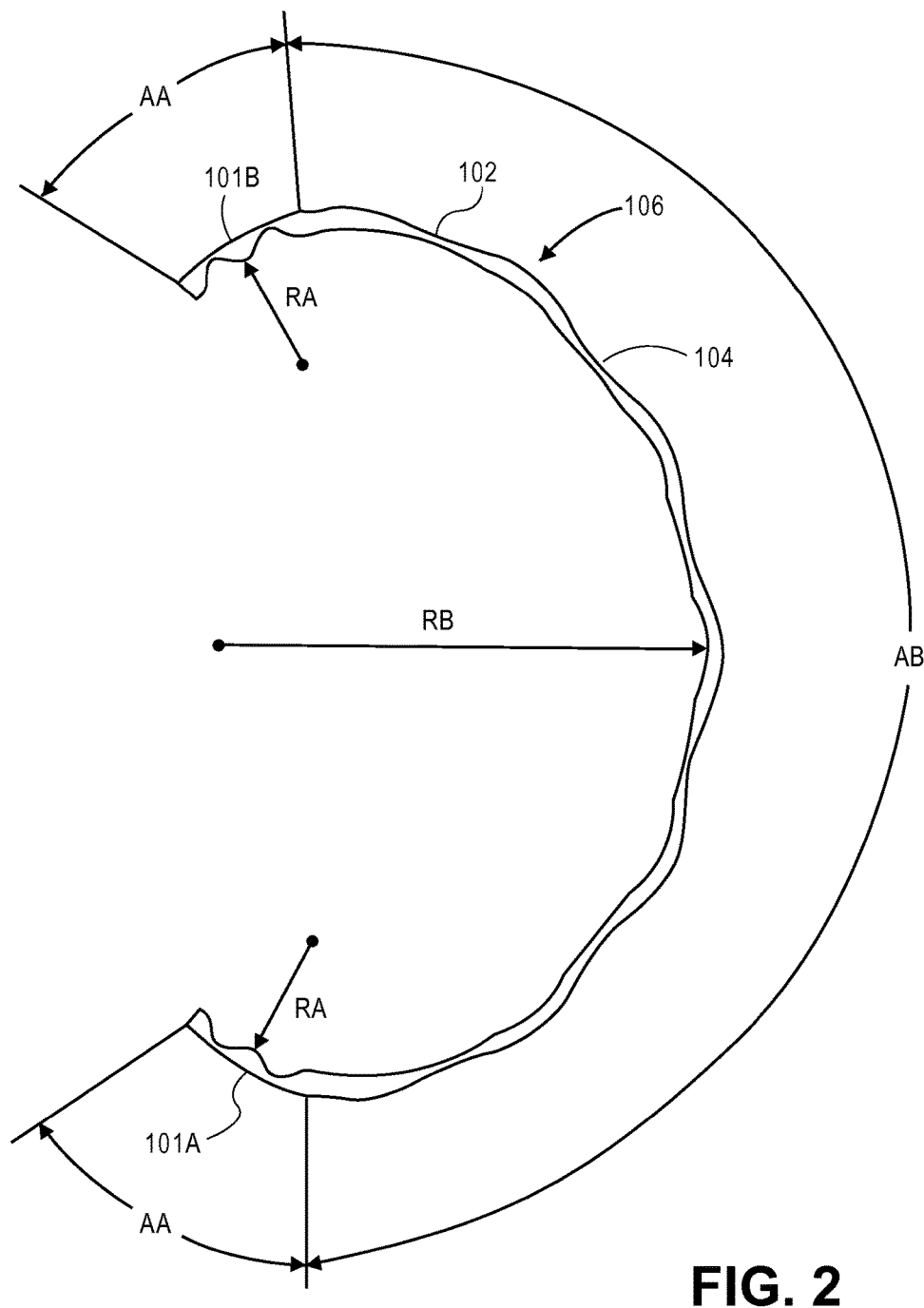
FIG. 2 is another drawing of the implant having a predetermined at rest shape.

The implant 100 may be biased to assume a predetermined at rest shape. This predetermined shape may include one or more bends or curves along the length of the implant. The predetermined shape can generally model the anatomy of the human eye, and in particular, the anatomy of Schlemm's canal into which it is to be implanted. FIG. 2 is a view of implant 100 assuming a predetermined at rest shape. As shown, the implant has an at rest shape that is generally curved. This at rest shape can be established, for example, using a heat-setting process. The shape of the implant in FIG. 2 can include a distal radius of curvature RA corresponding to each of the proximal and distal inlets 101A and 101B, and an intermediate or proximal radius of curvature RB corresponding to the intermediate portion of the implant between the inlets. The radius of curvature RB can approximate the curvature of Schlemm's canal, for example. In the embodiment of FIG. 2, the distal radii of curvature RA are smaller than the intermediate radius of curvature RB. For example, the distal radii of curvature RA can be approximately 0.105 inches and the intermediate radius of curvature RB can be approximately 0.215 inches. In the exemplary embodiment of FIG. 2, the distal radius of curvature RA corresponding to distal inlet 101A is approximately the same as the distal radius of curvature RA corresponding to inlet 101B. In some embodiments, however, the radius of curvature corresponding to distal inlet 101A can be different from the radius of curvature corresponding to inlet 101B.

As shown in FIG. 2, each of the proximal and distal inlets of the implant follow a radius of curvature RA along an arc extending across an angle AA. Similarly, an intermediate portion of the implant (i.e., the portion of the implant disposed between the distal and proximal inlets) follows a radius of curvature RB along an arc extending across an angle AB. In one embodiment, angle AA can be approximately 0-45 degrees and angle AB can be between approximately 60-180 degrees.

Various fabrication techniques may be used to fabricate the implant. For example, implant 100 can be fabricated by providing a generally flat sheet of material and laser cutting the material. The material may then be formed into a generally tubular shape as shown in FIG. 1. Any adjoining edges (such as edges 103) may be attached, such as by welding or other techniques known in the art. In another embodiment, the implant may be fabricated by providing a tube and laser cutting openings in the tube to form the shape shown in FIG. 1.

Implant 100 can be fabricated from various biocompatible materials possessing the necessary structural and mechanical attributes. Both metallic and non-metallic materials may be suitable. Examples of metallic materials include stainless steel, tantalum, gold, titanium, and nickel-titanium alloys known in the art as Nitinol. Nitinol is commercially available from Memry Technologies (Brookfield, Conn.), TiNi Alloy Company (San Leandro, Calif.), and Shape Memory Applications (Sunnyvale, Calif.).

The implant may include one or more therapeutic agents. One or more therapeutic agents may, for example, be incorporated into a polymeric coating that is deposited onto the outer surfaces of the struts and spines of the ocular implant. The therapeutic agent may comprise, for example, an anti-glaucoma drug. Examples of anti-glaucoma drugs include prostaglandin analogs. Examples of prostaglandin analogs include latanprost.

Figure 3A:
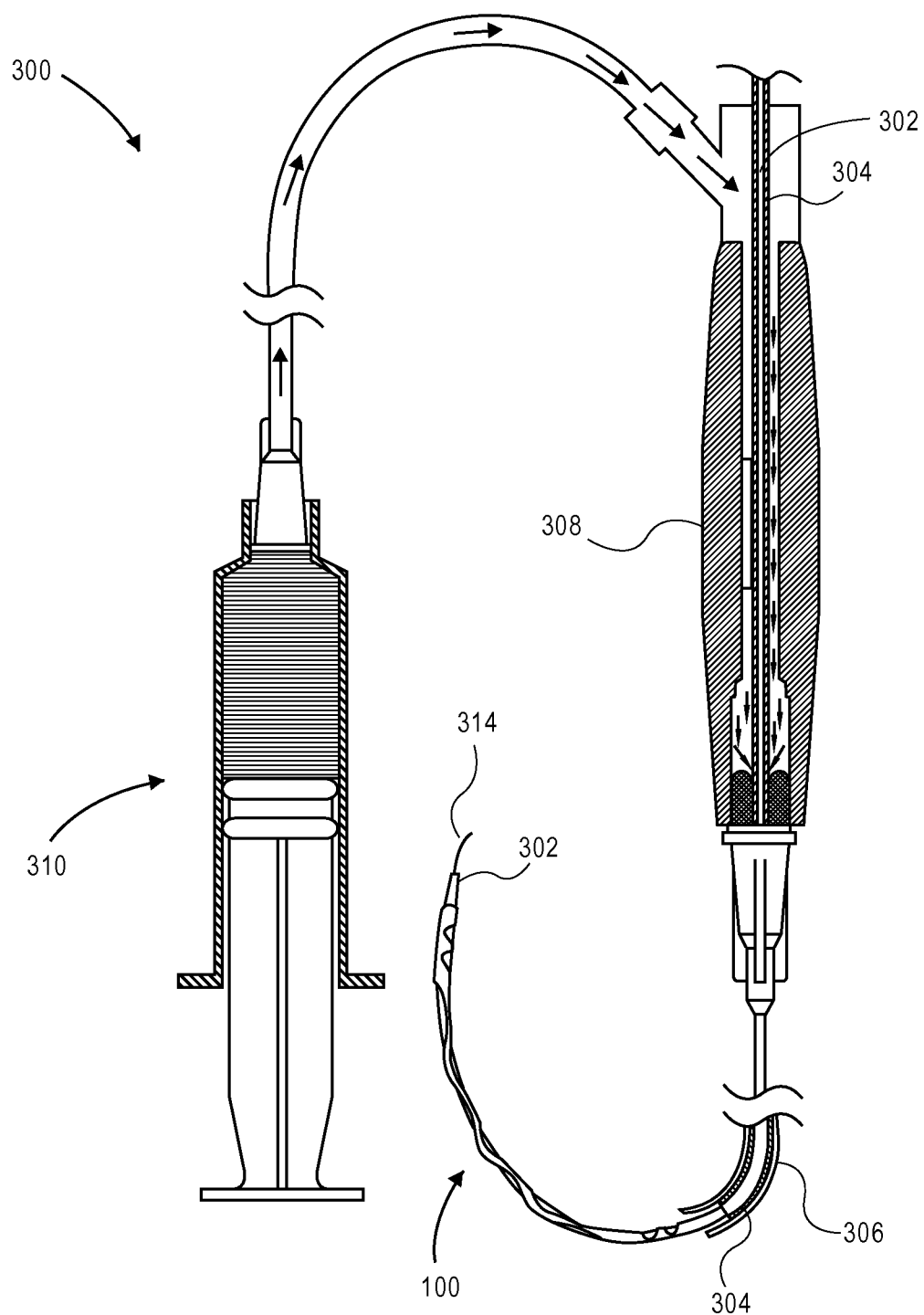
FIG. 3A is a drawing showing a delivery system for the ocular implant.

FIG. 3A is a partial view of a delivery system 300 used to deliver an implant 100 into the eye of a patient. The delivery system can comprise core 302, a push tube 304, cannula 306, handle 308, and guide wire 314. In some embodiments, the delivery system may optionally include a fluid source or syringe 310 in fluid communication with handle 308. In some exemplary methods, a syringe or other fluid source is used for flushing implant 100 with fluid to remove air bubbles and prevent the introduction of air bubbles into the anterior chamber of the eye. In some additional exemplary methods, a syringe or other fluid source may be used for injecting a viscoelastic into the eye for precluding the formation of a pool of blood near a target location.

Cannula 306 can be coupled to a distal end of handle 308. The cannula can be relatively straight, or as shown in FIG. 3A, can have a curved distal tip to aid in implanting implant 100 into an eye of a patient. In the embodiment of FIG. 3A, the distal end of cannula 306 is curved so as to pierce the trabecular mesh of a patient to gain access to Schlemm's canal. It should be noted that in FIG. 3A, illustration of the distal end of cannula 306 has been enlarged for ease of visualization and description.

Delivery system 300 may also include a mechanism (not shown in FIG. 3A), such as a thumb wheel, lever, or button on or near the handle 308 adapted to advance and retract core 302, push tube 304, and/or guide wire 314. This mechanism may also be used to retract core 302 relative to push tube 304 and/or guide wire 314. The implant may be moved in distal and proximal directions by moving core 302 and push tube 304 with the mechanism.

Figure 3B:
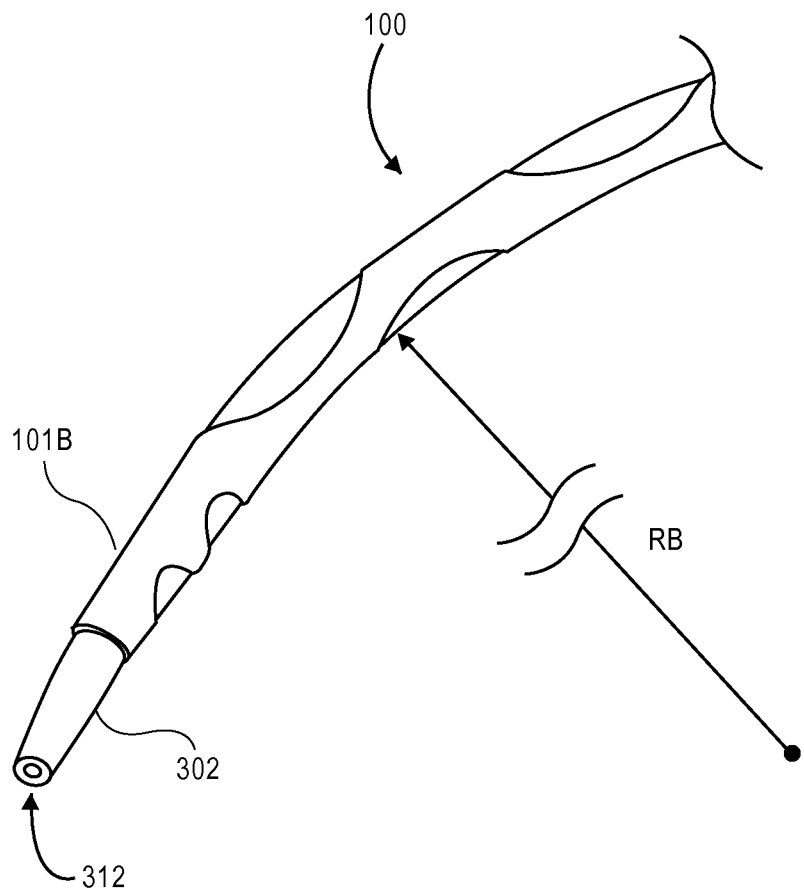
FIG. 3B is an enlarged view of a distal end of the implant mounted on a core.

As shown in FIG. 3B, implant 100 can be mounted on core 302. Core 302 can extend through a lumen defined by a push tube to extend through implant 100. In a preferred embodiment, core 302 extends beyond the distal end of the implant with a tapered finish. In another embodiment, the core extends only to the distal end of the implant. In a preferred embodiment, core 302 comprises polymeric tubing. In other embodiments, core 302 can be fabricated from similar materials to that of the implant, as described above. In general, the implant and core will comprise materials which provide a relatively low friction interface when placed in sliding contact with one another. Additionally, the materials are unlike to gall when placed in sliding contact with one another.

Among other features, one particular function of core 302 is to block the openings formed in implant 100 so as to minimize interference between the implant and tissue within Schlemm's canal as the implant is advanced during implantation. With reference to FIGS. 3A-3B, it can be seen that core 302 substantially fills implant 100. Together, core 302 and implant 100 form an assembly that presents a relatively smooth outer surface.

Another function of core 302 is to aid in the insertion of implant 100 into the eye of a patient. FIG. 3B shows a close up view of the distal tip of core 302 with implant 100 mounted on the core. As shown in FIG. 3B, the distal tip of core 302 is tapered and includes a guide wire lumen 312 which runs along the length of the core. The core can also be biased to assume a predetermined at rest shape corresponding to the predetermined shape of the implant 100 or any other desired predetermined shape. For example, an intermediate portion of core 302 can be biased to curve at a radius of curvature RB, which corresponds to radius of curvature RB of the intermediate portion of the implant in FIG. 2 as described above. Similarly, a distal or proximal portion of the core can be biased to curve at a radius of curvature RA, which corresponds to radius of curvature RA of the distal and proximal inlet portions of the implant. Despite the biased at rest shape of core 302, the core can be flexible enough to assume a generally straightened configuration when inserted into a delivery system or cannula for implantation into a patient, for example. If the core is biased to assume a predetermined at rest shape, then a portion of the core may be urged to assume a stressed shape when it is disposed in the implant.

Figure 3C:
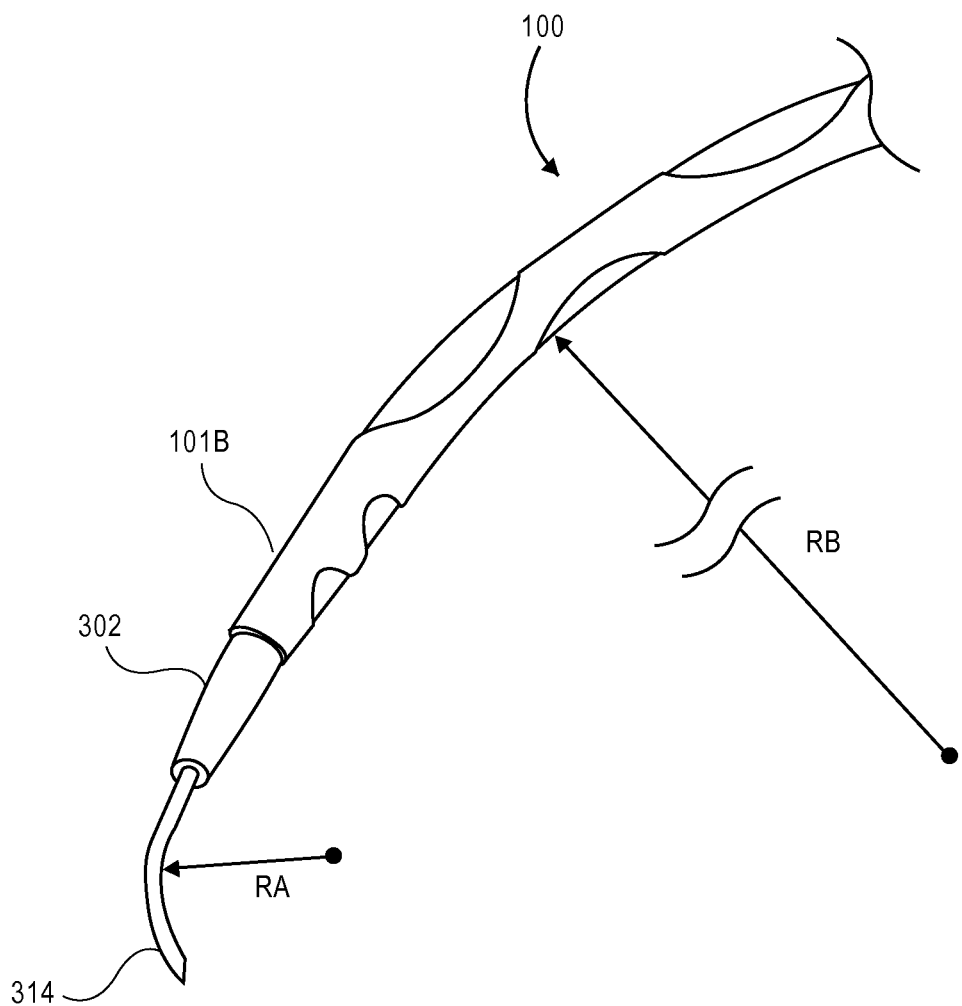
FIG. 3C is an enlarged view of the distal end of the implant mounted on a core further illustrating a tissue piercing guide wire.

FIG. 3C shows a close-up view of implant 100 mounted on core 302 and further including tissue piercing guide wire 314 adapted to advance and retract through the guide wire lumen of the core and extend out beyond the core. The guide wire can also include a tissue penetrating tip to allow the guide wire to cut through and penetrate tissue when desired. The guide wire can be a metallic wire, such as stainless steel, nitinol, MP-35N alloy or other appropriate materials. In one embodiment, the guide wire can have an approximate diameter of 0.004 inches. In general, the guide wire and core will comprise materials which provide a relatively low friction interface when placed in sliding contact with one another. Additionally, the materials are unlike to gall when placed in sliding contact with one another.

The distal end of guide wire 314 can also be biased to assume a predetermined at rest shape or curvature corresponding to the at rest shape of implant 100 or another desired at rest shape. For example, the distal tip of guide wire 314 can be biased to curve at a radius of curvature RA, which corresponds to radius of curvature RA of the distal and proximal inlet portions of the implant as shown in FIG. 2, and an intermediate portion of the guide wire can be biased to curve at a radius of curvature RB, which corresponds to radius of curvature RB of the intermediate portion of the implant, as described above. The radius of curvature RA can be smaller than the radius of curvature RB. In another embodiment, only the distal end of the guide wire can be biased to assume a predetermined at rest shape or curvature. Despite the biased at rest shape of guide wire 314, the guide wire is relatively flexible and can assume a generally straightened or slightly curved configuration when inserted into guide wire lumen 312 of core 302, for example.

This could cause a portion of the guide wire to be urged to assume a stressed shape when it is disposed in the core, such as when a distal portion of the guide wire is disposed in an intermediate portion of the core, and cause the portion of the guide wire to assume the predetermined at rest shape when it is advanced distally from the core, such as when the distal portion is advanced distally from the core, for example. The stressed shape is generally straighter than the predetermined at rest shape. It should be noted that the guide wire can be correctly oriented relative to the anterior chamber because the predetermined shape of the guide wire can self align to Schlemm's canal creating an automatic alignment of the distal radius of curvature of the guide wire.

In some useful embodiments, the relaxed shape of the guide wire is selected so that so that a distal portion of the guide wire extends into the anterior chamber when a longitudinal axis of the proximal portion of the guide wire is generally coaxial with a longitudinal axis of Schlemm's canal and the distal radius of curvature of the guide wire is free to assume its relaxed shape. The guide wire tends to orient itself within the core so that a plane defined by a longitudinal axis of the guide wire is coplanar with a plane defined by the longitudinal axis of Schlemm's canal.

A method of implanting implant 100 into a patient will now be described with reference to FIGS. 4-9. The implant described herein is adapted to be implanted into a patient's eye so that both the distal and proximal inlets are positioned in the anterior chamber of the eye while the remaining portion of the implant is positioned in Schlemm's canal. This facilitates the flow of aqueous humor out of the anterior chamber of the eye through both inlets into Schlemm's canal, and then out of Schlemm's canal via natural outlets communicating with the canal. An implant as described herein advantageously provides for multiple fluid inlets, allowing the implant to facilitate flow of aqueous humor into Schlemm's canal even if one of the inlets fails to function or becomes clogged.

Figure 4:
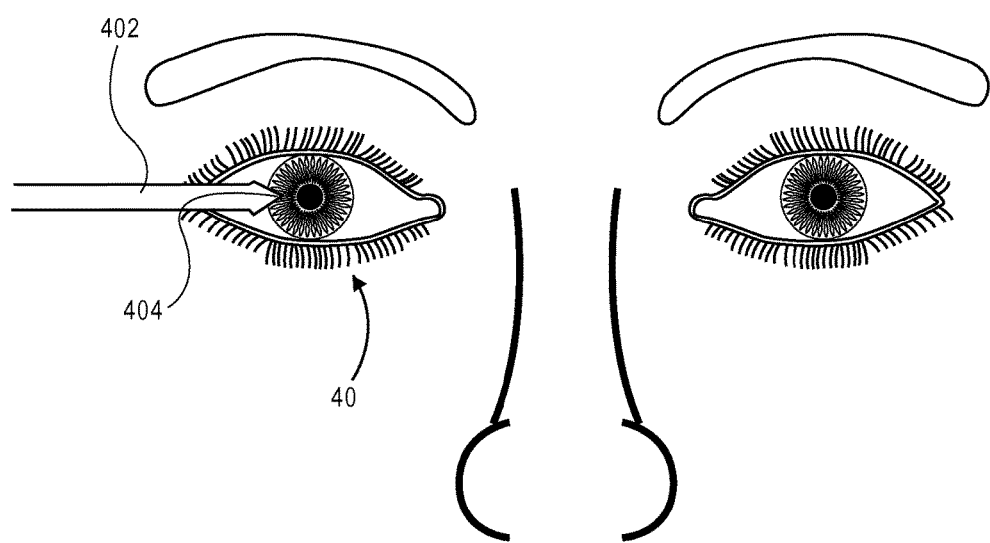
FIG. 4 is a simplified view showing a human face including a pair of eyes.
Figure 5:
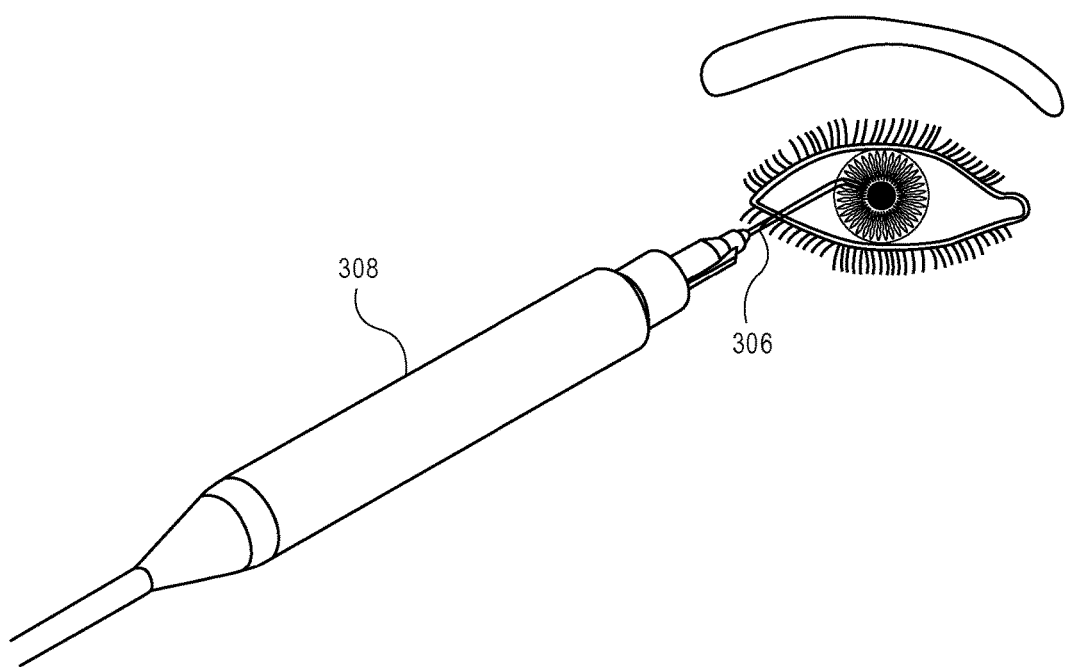
FIG. 5 is an additional view of the eye shown in the FIG. 4 further illustrating a cannula inserted into the eye.

FIG. 4 is a simplified drawing showing a human face including an eye 40. In FIG. 4, a surgeon can use a scalpel or knife 402 to make an incision 404 through the cornea of the eye. FIG. 5 is an additional view of the eye shown in the previous figure. In FIG. 5, the distal tip of cannula 306 can be inserted through the incision in the cornea.

Figure 6:
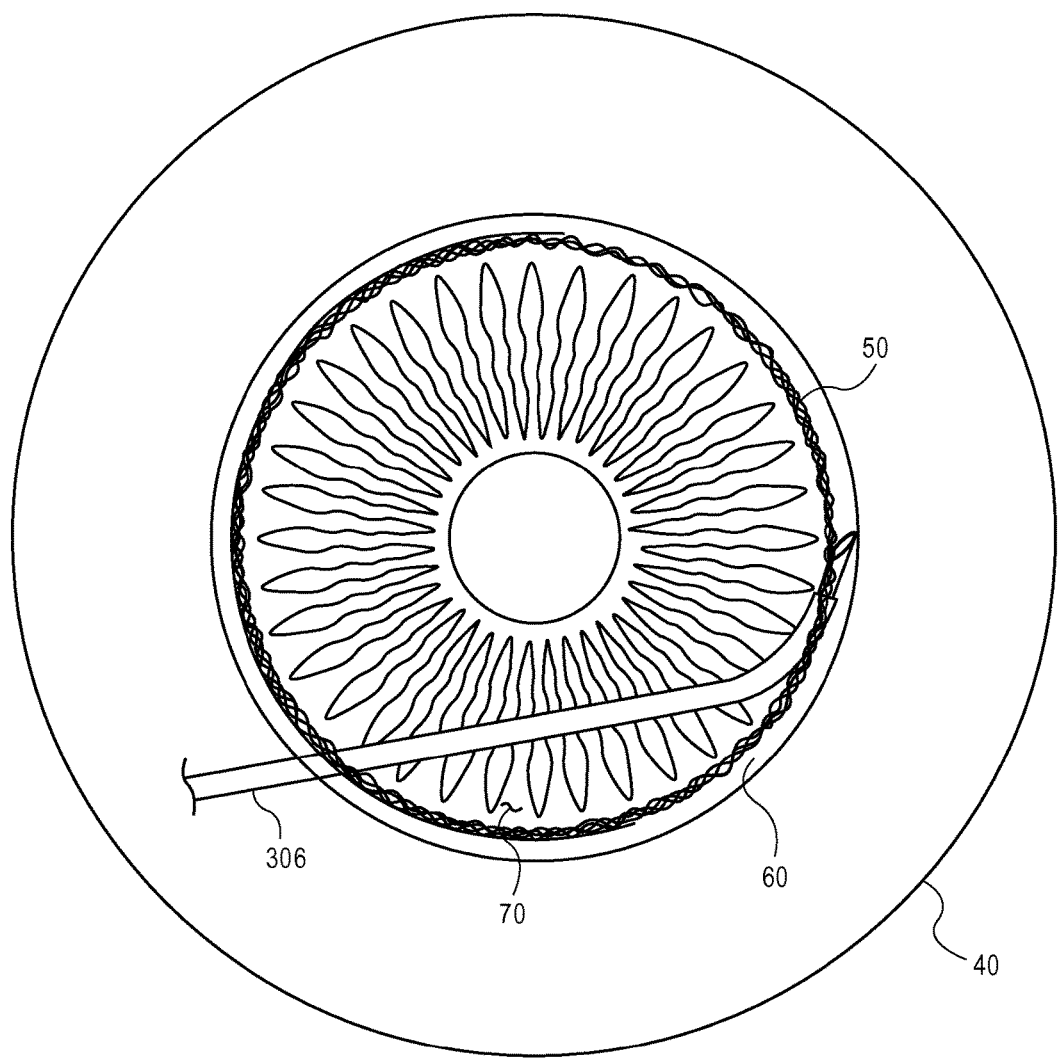
FIG. 6 is an enlarged view of the eye shown in FIG. 5 further showing the cannula piercing the trabecular mesh and Schlemm's canal.

FIG. 6 is a further enlarged view of eye 40. In FIG. 6, the distal tip of cannula 306 has pierced through trabecular mesh 50 and through the wall of Schlemm's canal 60. When the distal tip of cannula 306 pierces through these tissues, it places Schlemm's canal in fluid communication with the anterior chamber 70 of eye 40. As shown, the distal tip of cannula 306 can be curved to achieve tangential entry into Schlemm's canal. However, in other embodiments the cannula can be relatively straight.

When the distal tip of the cannula pierces the tissues separating Schlemm's canal from the anterior chamber, a small amount of blood may flow from the venous system into Schlemm's canal. This blood will typically cause Schlemm's canal to turn a red/pink color which can enhance the visibility of Schlemm's canal for a short time (i.e., until the blood in Schlemm's canal dissipates). It may be desirable to advance an implant into Schlemm's canal while the presence of blood in the canal is enhancing the visibility of the canal.

In some cases, however, blood will leak out of the puncture made by the distal end of the cannula. When this is the case, the blood may pool around the opening of the puncture and interfere with the physician's ability to see the opening. Methods described herein may be used to displace any blood that is pooled around the opening of the puncture. Methods described herein may also be used to preclude blood from pooling around the opening of a puncture.

Blood can be precluded from pooling near an anticipated puncture by injecting a bolus of viscoelastic near the place where the puncture will be made. Blood that has entered the anterior chamber may be displaced, for example, by injecting a bolus of viscoelastic near the place where the cannula has punctured the trabecular mesh. Various fluids may be used in conjunction with the methods described in this document. Examples of fluids that may be suitable in some applications include water, saline, hyaluronic acid and/or viscoelastic. The term "viscoelastic" is sometimes used to describe various viscoelastic materials that are injected into the eye as part of a surgical procedure. Viscoelastics for use in ophthalmic surgery are commercially available from Bausch and Lomb Incorporated (Rochester, N.Y., U.S.A.) and Alcon, Incorporated (Hünenberg, Switzerland). Viscoelastics may comprise, for example, hyaluronic acid. Hyaluronic acid is a material that is naturally found in the vitreous humor that fills the posterior chamber of the eye. Accordingly, this material is well suited for use in ophthalmic surgery. Hyaluronic acid is also known as hyaluronan and hyaluronate.

Figure 7:
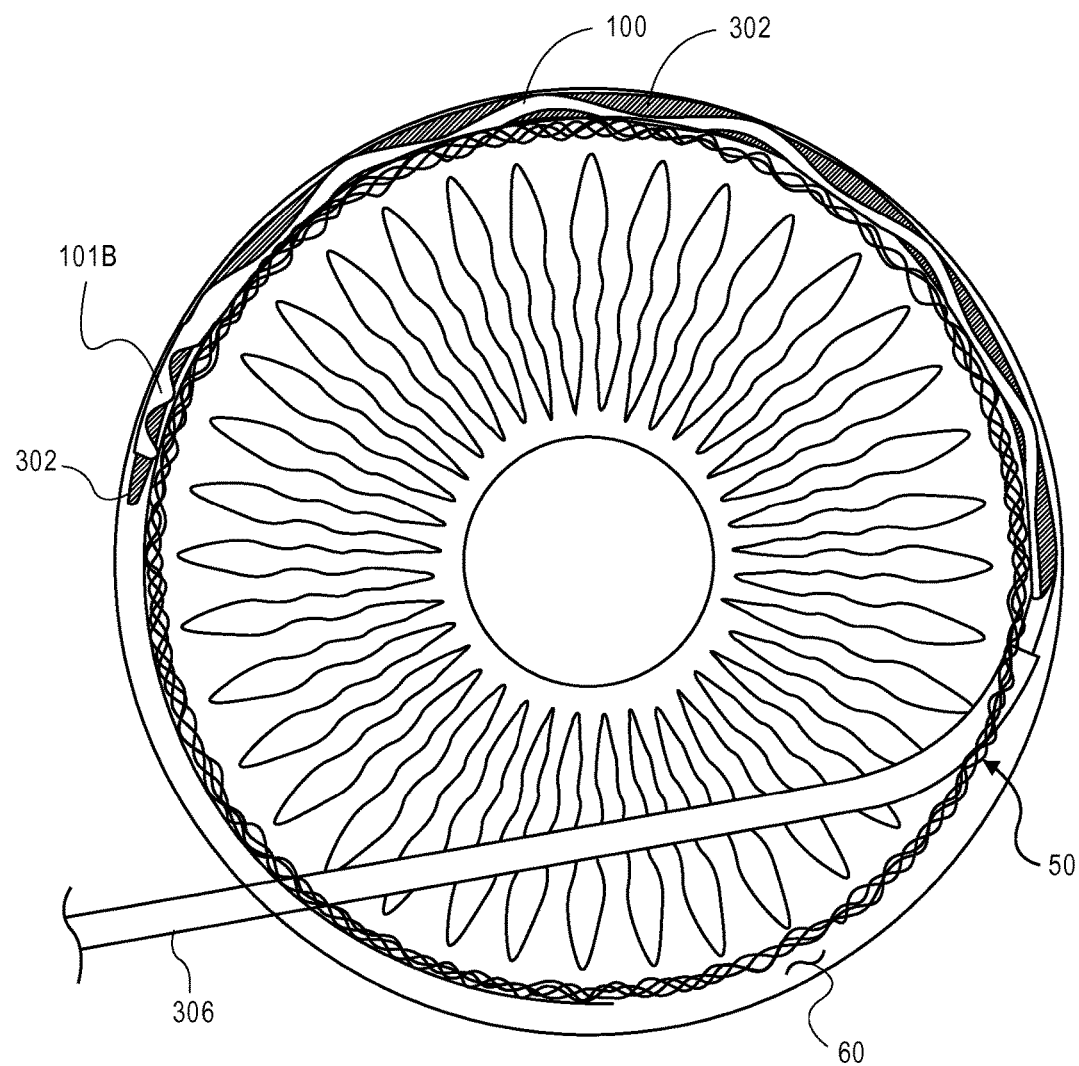
FIG. 7 is a further enlarged view of an eye further illustrating an implant partially inserted into Schlemm's canal.

FIG. 7 is a further enlarged view of the eye shown in FIG. 6 with an implant partially inserted into the eye. During delivery, implant 100 can be mounted on core 302 which is movable with implant 100, as described above. Among other features, one particular function of core 302 is to block the openings in implant 100 so as to minimize interference between the implant and tissue within Schlemm's canal as the implant is advanced. As described above, distal inlet portion 101B is situated at the distal end of implant 100, and core 302 extends beyond the distal inlet a small distance to a tapered finish. In a preferred embodiment, the entire length of the tapered end of core 302 extends distally beyond implant 100. The tapered finish of the core can be provided to facilitate dilation of tissue in Schlemm's canal while minimizing the compressive forces necessary to advance the implant in the canal.

A push tube can be engaged with a proximal end of implant 100. The push tube may be used to apply distally directed force to the proximal end of the implant 100 to advance the implant into Schlemm's canal. Core 302 can extend proximally into the push tube during implantation. A handheld actuator or mechanism (not shown) may be used to provide relative motion to the push tube, the core, and or the guide wire. When the implant is being inserted into Schlemm's canal, the tissue piercing guide wire can be positioned within the guide wire lumen, but should not extend out beyond the core to avoid cutting or penetrating tissue.

As shown in FIG. 7, the implant can be inserted into Schlemm's canal with the push tube until the distal inlet portion 101B of implant 100 is in a desired position with respect to the proximal inlet or proximal portion of the implant. In FIG. 7, the distal inlet is positioned approximately 180 degrees from the proximal inlet of the implant, which at this point in the procedure is still positioned within cannula 306. In other embodiments, the distal inlet may be positioned at different positions with respect to the proximal inlet depending on the length of the implant, typically anywhere from 60 to 180 or more degrees apart.

Figure 8A:
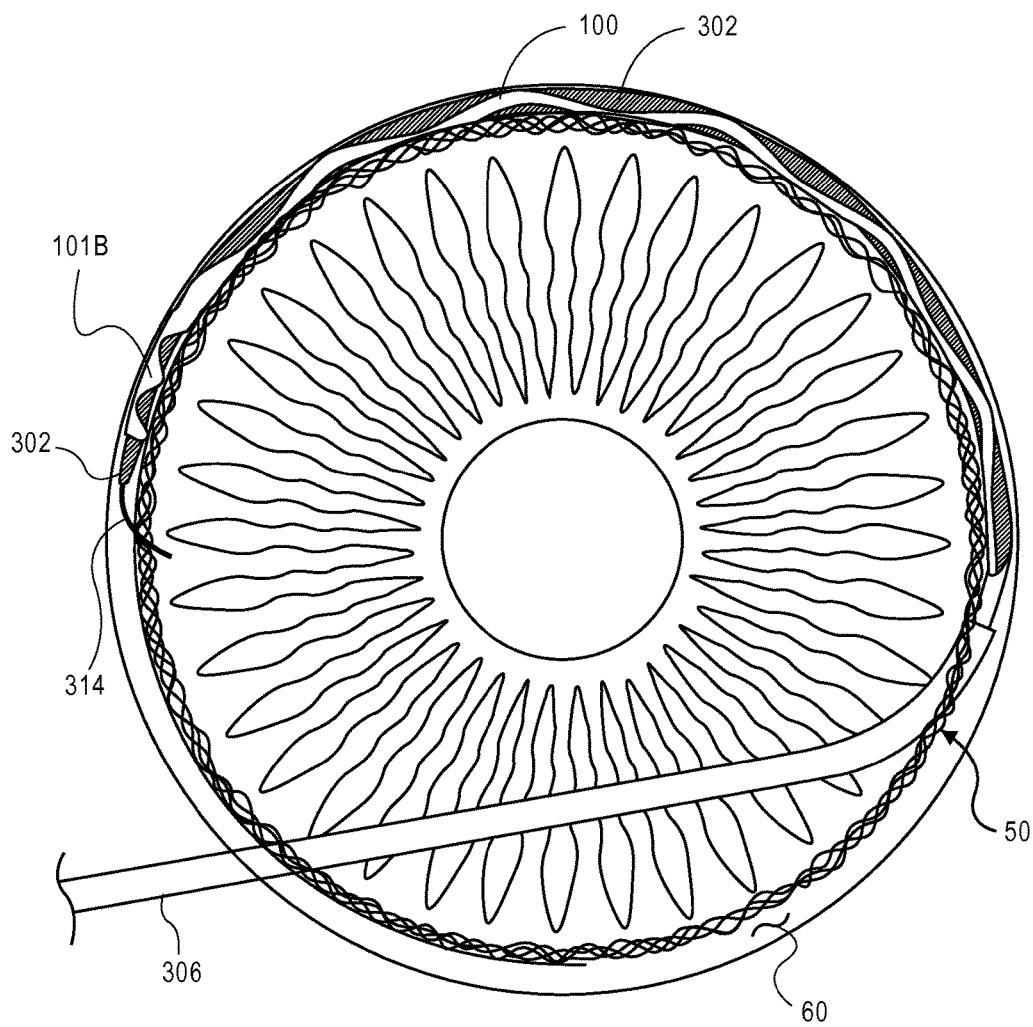
FIG. 8A is an additional view of the eye shown in FIG. 7 further illustrating a guide wire penetrating the tissues of the eye into the anterior chamber.

At this point in the implantation procedure the distal inlet 101B can be re-inserted into the anterior chamber of the eye using one of several methods. A first method is illustrated in FIG. 8A. As shown in FIG. 8A, tissue piercing guide wire 314 can be extended distally from core 302. In some useful embodiments, the relaxed shape of the guide wire is selected so that a distal portion of the guide wire extends into the anterior chamber when a longitudinal axis of the proximal portion of the guide wire is generally coaxial with a longitudinal axis of Schlemm's canal and the distal radius of curvature of the guide wire is free to assume its relaxed shape. The guide wire tends to orient itself within the core so that a plane defined by a longitudinal axis of the guide wire is coplanar with a plane defined by the longitudinal axis of Schlemm's canal.

Figure 9:
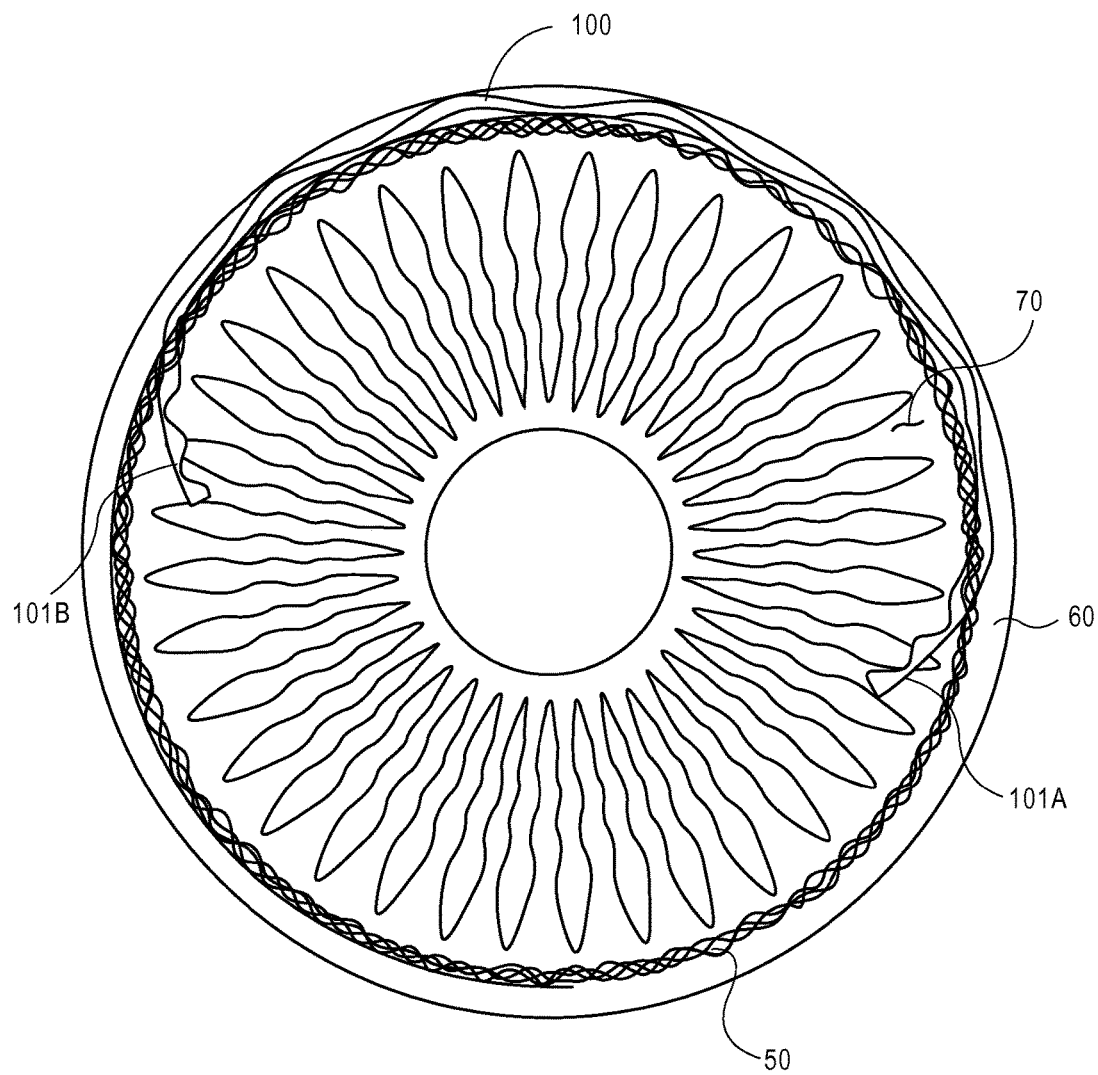
FIG. 9 is a view of an eye with an implant having two inlets positioned in the anterior chamber and the remaining portion of the implant positioned in Schlemm's canal.

As described above, the distal end of the guide wire 314 can have a pre-biased radius of curvature RA, which can be smaller than the radius of curvature RB of the portion of implant 100 within Schlemm's canal. Thus, when the guide wire is extended beyond the core, the guide wire will be biased to curve inwards back into the anterior chamber of the eye. The tissue piercing distal tip of the guide wire can allow the guide wire to penetrate the tissues of Schlemm's canal and the trabecular meshwork to gain access to the anterior chamber. Once access to the anterior chamber has been achieved with the guide wire, the implant and core can be advanced together over the guide wire to position distal inlet 101B properly within the anterior chamber. The taper of the core will facilitate placement of the implant by dilating an opening through the meshwork. The implant can then be advanced into the anterior chamber and location can be achieved which allows both inlets to extend equally and uniformly from the canal. Next, the guide wire 314 can be removed from the core 302, the core can be removed from implant 100, and cannula 306 can be removed from over the implant and out of the eye, leaving proximal inlet 101A and distal inlet 101B in the anterior chamber, and the remaining portion of implant 100 in Schlemm's canal, as shown in FIG. 9.

When the proximal and distal inlets are positioned in the anterior chamber, they effectively serve as anchors or locks to reduce the likelihood that the intermediate portion of the implant will migrate or move within Schlemm's canal or that the inlets will become dislodged or removed from the anterior chamber. This is because the proximal and distal inlets extend at a radially inward direction relative to the arcuate path of the longitudinal axis of the intermediate portion, which can be shaped to fit the contours of Schlemm's canal.

Figure 8B:
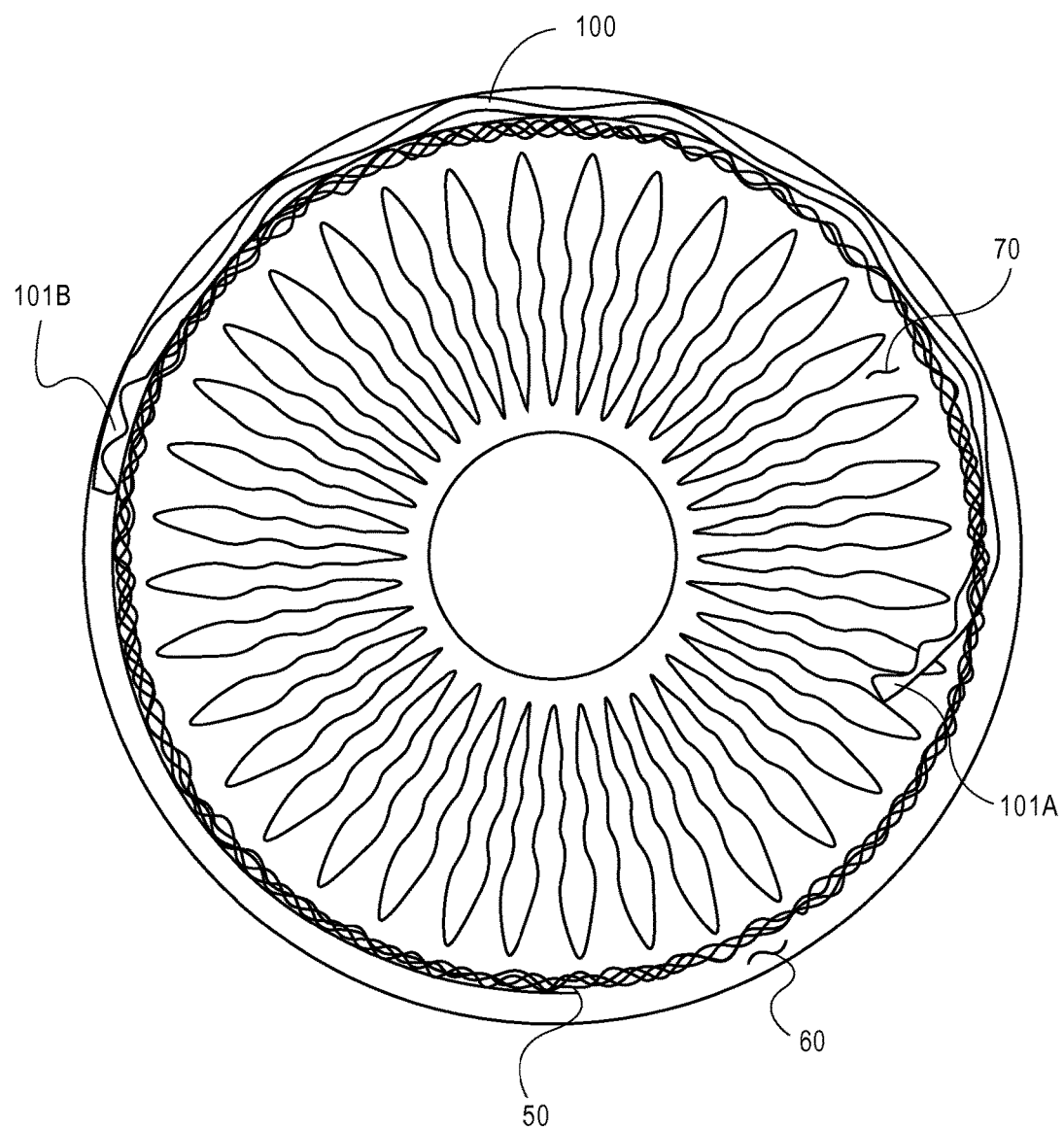
FIG. 8B is a view of the eye shown in FIG. 7 further illustrating a proximal inlet of an implant in the anterior chamber and a distal inlet of the implant in Schlemm's canal.
Figure 8C:
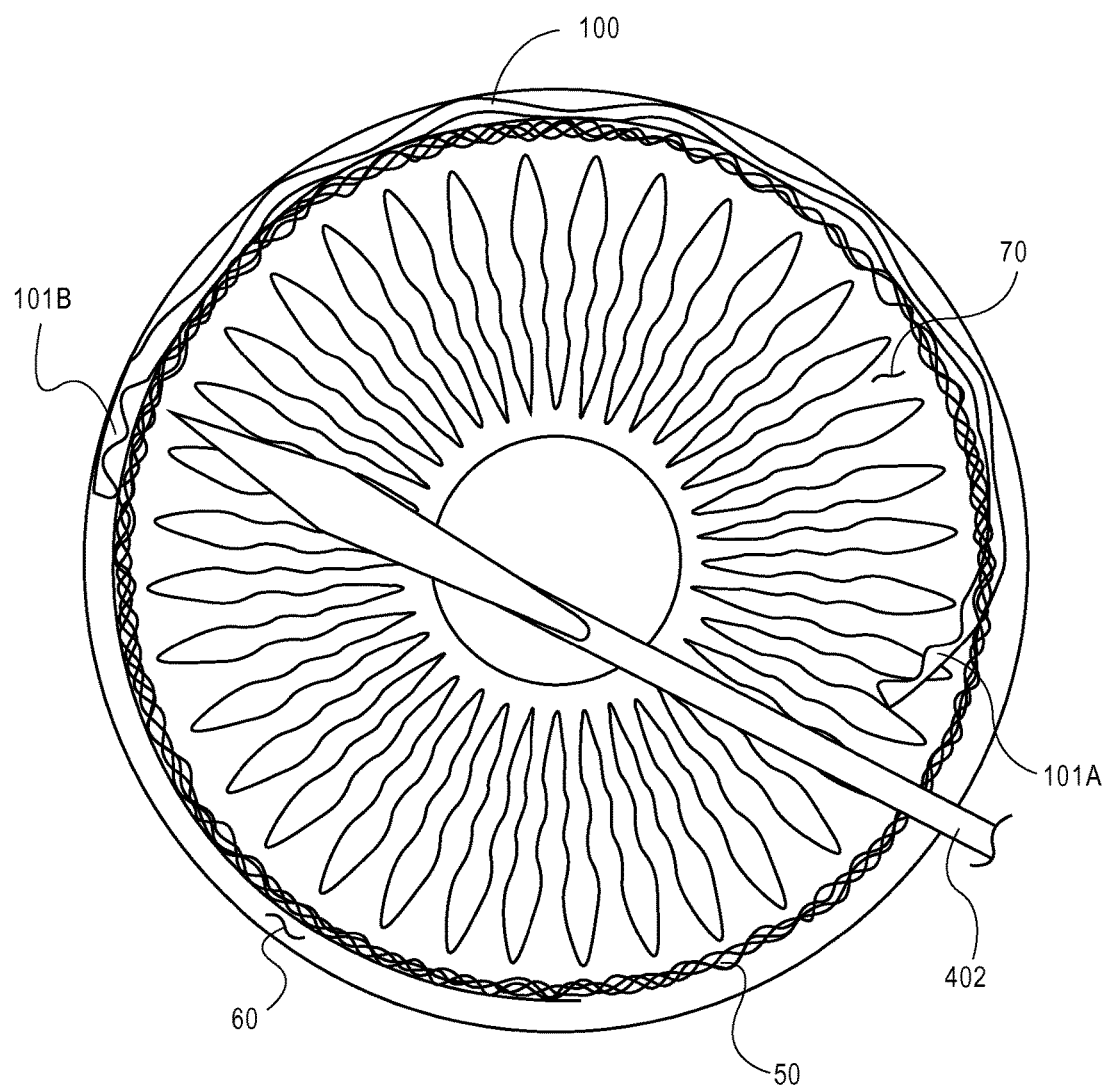
FIG. 8C is a view of the eye shown in FIG. 8B further illustrating making an incision near the distal inlet of the implant.

Other methods of inserting distal inlet 101B into the anterior chamber are illustrated in reference to FIGS. 8B and 8C. It should be noted that this method may be performed with or without the use of guide wire 314. If guide wire 314 is used, it can be removed from the core 302, the core can be removed from implant 100, and cannula 306 can be removed from over the implant and out of the eye, leaving proximal inlet portion 101A in the anterior chamber, and distal inlet 101B and the remaining portion of implant 100 in Schlemm's canal. Removing the core from the implant can cause the distal inlet to bias inwards to the predetermined at rest shape, as described above. In some applications, the distal inlet may push through the tissues of Schlemm's canal and the trebecular meshwork to enter the anterior chamber when the implant assumes its at rest shape. In some cases, it may be desirable to make an incision in the tissues proximate the distal inlet. When this is the case, the incision may be made, for example, with a scalpel. In some embodiments, the implant may include a cutter that is capable of making the incision. In one embodiment, the distal inlet 101B can have a self-piercing distal tip. Advancing the self-piercing distal tip in a distal direction when the distal inlet is biased inwards can cause the distal inlet to cut through the tissues of Schlemm's canal and the trabecular meshwork to gain entry into the anterior chamber.

In another embodiment, as shown in FIG. 8C, instead of having a self-piercing distal tip, a surgeon can make an incision near the distal inlet portion with scalpel 402. As described above, the portion of implant 100 near distal inlet 101B is biased to assume a predetermined at rest shape or curvature with a radius of curvature RA, as shown in FIG. 2. Thus, when the incision is made near the distal inlet, the distal portion of the implant comprising the distal inlet will bend inwards to assume the predetermined at rest shape, which results in the distal inlet 101B positioning itself within the anterior chamber of the eye. As a result, the distal and proximal inlets will be positioned in the anterior chamber of the eye, and the remaining portion of the implant will be positioned in Schlemm's canal, as shown in FIG. 9. In yet another embodiment, a surgeon can reach through the trabecular meshwork to grab the implant with a surgical device, such as forceps, to pull the implant from Schlemm's canal back into the anterior chamber.

Figure 8D:
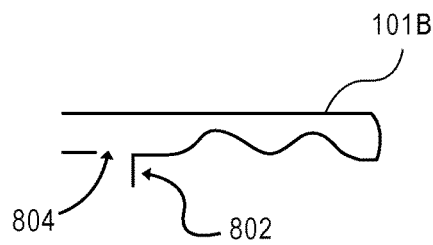
FIGS. 8D-8K are some embodiments of implants comprising a self-piercing distal inlet.

Other embodiments of a self-piercing distal inlet are illustrated in FIGS. 8D-8K. FIG. 8D illustrates a distal inlet 101B with a cutter 802 extending radially from the distal inlet. The cutter can be configured to swing or "spring" outwards from hole 804, such as with a heat-set or shape-set design. For example, the cutter can be shape set with a predetermined body transition temperature which would cause the cutter to spring outwards from the hole when the implant is heated to the predetermined body transition temperature. However, it should be understood that the cutter can be designed to swing outwards without requiring the implant to be heated.

Figure 8E:
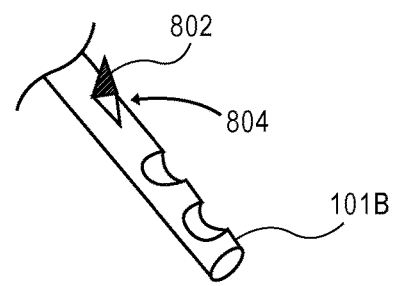
Figure 8F:
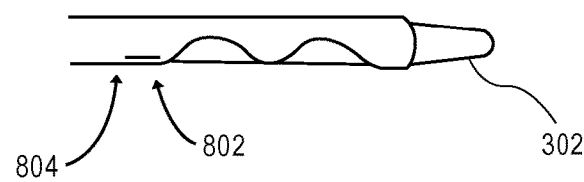

FIG. 8E is a top down view of distal inlet 101B further showing another view of cutter 802 and hole 804. In one embodiment, as shown in FIG. 8F, the cutter 802 can be tucked inside and held in place within the distal inlet when core 302 is inserted into the implant. Upon removal of the core, the cutter can swing outwards into the position shown in FIG. 8D.

Figure 8G:
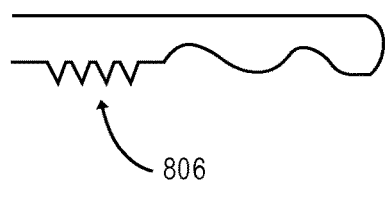
Figure 8H:
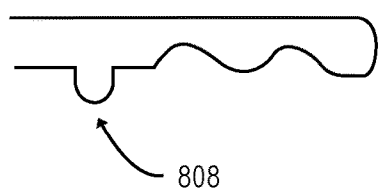

As shown in FIG. 8E, cutter 802 can be a triangular shape. Other variations on the design can also be used, such as a serrated edge cutter 806, as shown in FIG. 8G, a rectangular cutter, a semicircular shaped cutter 808, as shown in FIG. 8H, or any other appropriately shaped cutter as long as the cutter is sharp enough to penetrate through tissue. In the embodiment of a serrated cutter, the trabecular meshwork and Schlemm's canal can be cut by moving the implant back and forth to slice through tissue and introduce the implant into the anterior chamber, for example.

Figure 8I:
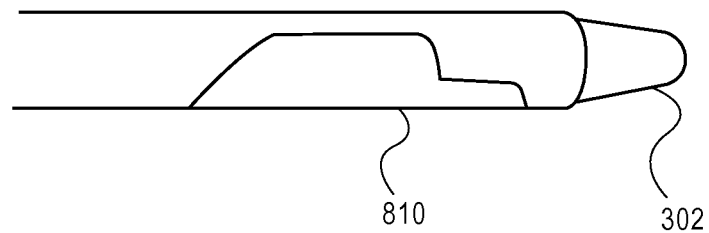
Figure 8J:
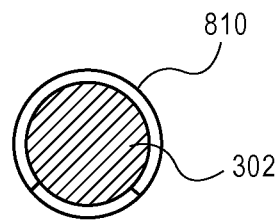
Figure 8K:
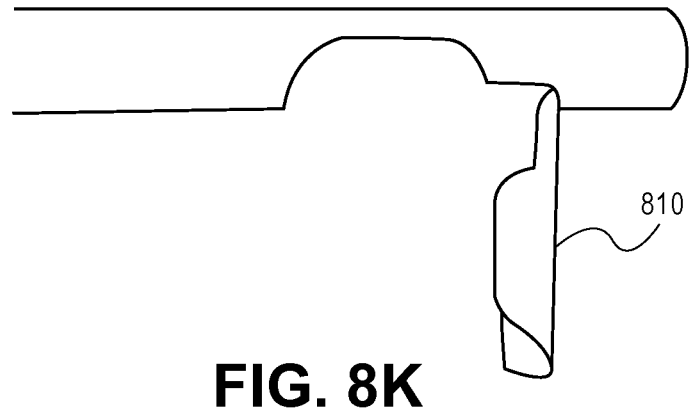

FIGS. 8I-8K show an alternative embodiment of a self-piercing distal inlet having a hatch 810 that engages the core 302. The hatch comprises an arm that hingedly connects the hatch to the implant. In FIG. 8I, when core 302 is disposed within the implant, it engages hatch 810 to cause the hatch to be flush with the body of the implant, so that the hatch is generally coaxial with the implant. FIG. 8J illustrates a cross section of hatch 810 being flush with the implant while core 302 is disposed in the implant. It can be seen that at least a portion of the hatch extends around a portion of the core across a radial span of more than 180 degrees. When the core is removed from the implant, the hatch can be heat set or shape set to assume a predetermined shape, as shown in FIG. 8K.

In FIG. 8K, hatch 810 is shown in a fully extended or "swung out" position due to removal of the core from the implant. This extended position causes the hatch to be skewed relative to the longitudinal axis of the implant. The hatch can be biased to assume this extended position, for example. The hatch can have a sharp tip or edge to slice through tissue, such as Schlemm's canal and/or the trabecular meshwork, to gain access to the anterior chamber of the eye.

Figure 10:
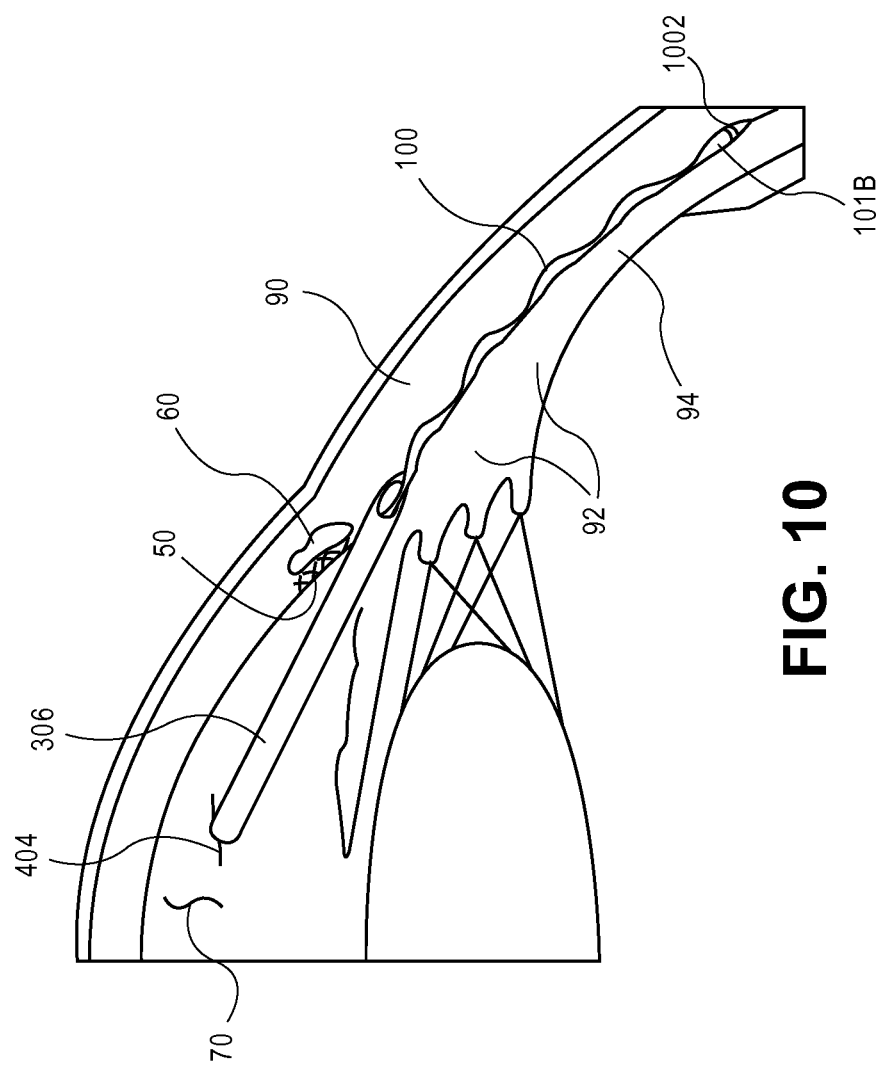
FIG. 10 is a view of an ocular implant with a distal end positioned in the suprachoroidal space of the eye.

In FIG. 10, a cannula 306 is shown extending through an incision 404 in the cornea of an eye. In the embodiment of FIG. 10, an implant 100 has been advanced into the eye so that a distal end of the implant is disposed in the suprachoroidal space 1002 of the eye. FIG. 10 also includes a view of sclera 90, ciliary body 92, and choroid 94 of the eye. The distal end of the implant can be distal inlet 101B, as described above. In another embodiment, the distal end of the implant does not have to be distal inlet 101B, but rather can share the same structural design as an intermediate portion of the implant, as described above. A method associated with inserting implant 100 into the suprachoroidal space 1002 of the eye can include the various delivery system components described herein, including core 302, cannula 306, and guide wire 314, for example.

Figure 11:
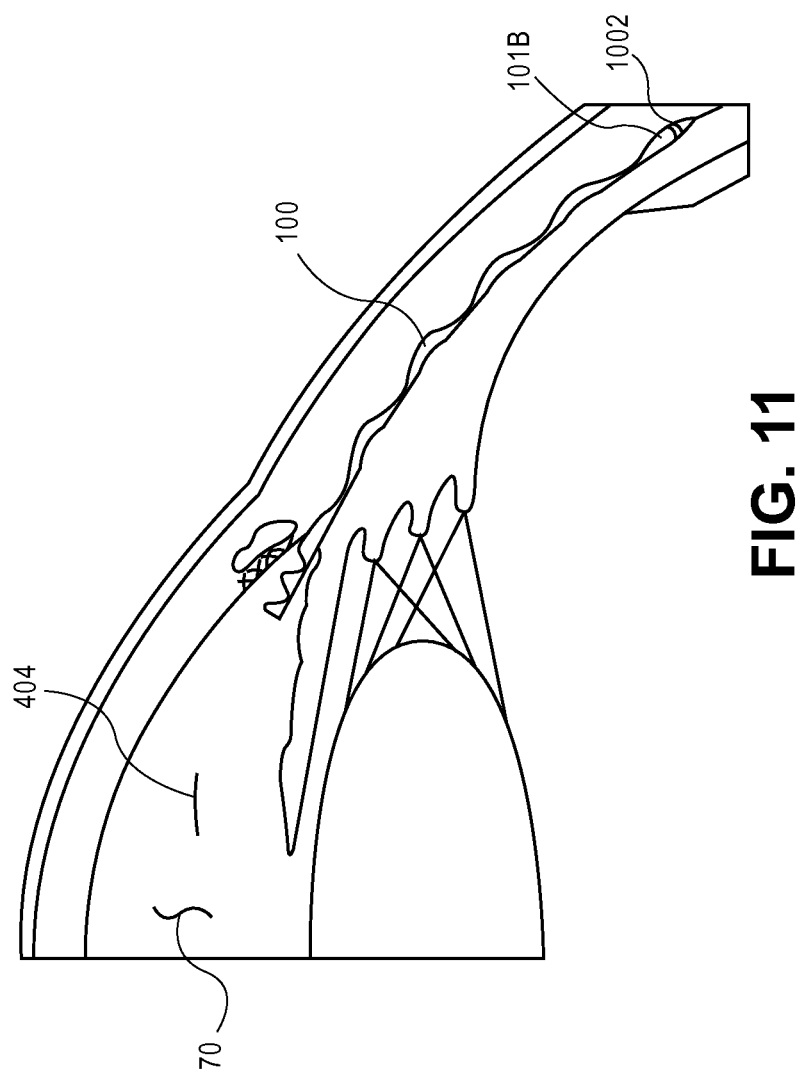
FIG. 11 is another view of the ocular implant with a distal end positioned in the suprachoroidal space of the eye.

FIG. 11 is an additional partial cross-sectional view of the eye shown in the previous figure. In the embodiment of FIG. 11, the cannula has been withdrawn from anterior chamber 70 and incision 404 in the cornea has closed. Implant 100 is positioned so that its distal end is disposed in suprachoroidal space 1002 of the eye and the proximal end of implant 100 is disposed in the anterior chamber. When this is the case, aqueous humor can flow along the surface of implant 100. In this way, implant 100 allows aqueous humor to leave anterior chamber 70 and enter suprachoroidal space 1002. Numerous veins and arteries are located in suprachoroidal space. Accordingly, aqueous humor entering the suprachoroidal space can be absorbed into the bloodstream by passing through the walls of small blood vessels. This excess aqueous humor can then be carried away be venous blood leaving the eye.

In the methods described above, the predetermined shape of the implant, core, and/or guide wire will typically self align the implant in Schlemm's canal. However, the implant may additionally be rotated within Schlemm's canal to attain the appropriate orientation.

While exemplary embodiments of the present invention have been shown and described, modifications may be made, and it is therefore intended in the appended claims to cover all such changes and modifications which fall within the true spirit and scope of the invention.

What is claimed is:

1. A method of facilitating movement of aqueous humor from an anterior chamber into Schlemm's canal, the method comprising:
    supporting a first opening in trabecular mesh tissue and a second opening in trabecular mesh tissue with an implant;
    flowing aqueous humor from the anterior chamber into a first inlet of the implant into an elongate longitudinal open channel extending through the first opening into an intermediate portion of the implant disposed in Schlemm's canal; and
    flowing aqueous humor from the anterior chamber into a second inlet of the implant and through the second opening into the elongate longitudinal open channel in the intermediate portion.

2. The method of claim 1 further comprising flowing aqueous humor from the intermediate portion of the implant into natural outlets of the eye communicating with Schlemm's canal.

3. The method of claim 2 further comprising flowing aqueous humor radially outward from the elongate longitudinal open channel through a longitudinal opening in the implant into the natural outlets.

4. The method of claim 1 further comprising flowing aqueous humor through the implant longitudinally along Schlemm's canal.

5. The method of claim 1 further comprising supporting Schlemm's canal tissue with the intermediate portion of the implant.

6. The method of claim 1 wherein the first inlet is disposed at a first end of the implant and the second inlet is disposed at a second end of the implant.

7. The method of claim 6 wherein the implant is curved, the first inlet being spaced 60 to 180 degrees from the second inlet.

8. A method of facilitating movement of aqueous humor from an anterior chamber into Schlemm's canal, the method comprising:
    supporting a first opening in trabecular mesh tissue at a first location and a second opening in trabecular mesh tissue at a second location with an implant;
    flowing aqueous humor from the anterior chamber into a first inlet disposed at a first end of the implant into an elongate longitudinal channel extending through the first opening into an intermediate portion of the implant disposed in Schlemm's canal; and
    flowing aqueous humor from the anterior chamber into a second inlet of the implant disposed at a second end of the implant and through the second opening into the elongate longitudinal channel in the intermediate portion.

9. The method of claim 8 further comprising flowing aqueous humor from the intermediate portion of the implant into natural outlets of the eye communicating with Schlemm's canal.

10. The method of claim 9 further comprising flowing aqueous humor radially outward from the elongate longitudinal open channel through a longitudinal opening in the implant into the natural outlets.

11. The method of claim 8 further comprising flowing aqueous humor through the implant longitudinally along Schlemm's canal.

12. The method of claim 8 further comprising supporting Schlemm's canal tissue with the intermediate portion of the implant.

13. The method of claim 8 wherein the implant is curved, the first inlet being spaced 60 to 180 degrees from the second inlet.

* * * * *